(12) United States Patent
Lehmann et al.

(10) Patent No.: US 6,323,199 B1
(45) Date of Patent: Nov. 27, 2001

(54) NONSTEROIDAL ANTI-INFLAMMATORY AGENTS

(75) Inventors: Manfred Lehmann; Konrad Krolikiewicz; Werner Skuballa; Peter Strehlke; Frank Kalkbrenner; Roland Ekerdt; Claudia Giesen, all of Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/448,278

(22) Filed: Nov. 24, 1999

(30) Foreign Application Priority Data

Nov. 27, 1998 (DE) .................................. 198 56 475

(51) Int. Cl.⁷ ........................ A61K 31/535; A61K 31/34
(52) U.S. Cl. ....................................... 514/230.5; 514/470
(58) Field of Search ................... 514/230.5, 470

(56) References Cited

U.S. PATENT DOCUMENTS

| | | |
|---|---|---|
| 4,780,469 | 10/1988 | Toda et al. |
| 4,847,275 | 7/1989 | Toda et al. |
| 4,880,839 | 11/1989 | Tucker . |
| 4,939,141 | 7/1990 | Toda et al. |
| 5,446,058 | 8/1995 | Toda et al. |
| 5,459,134 | 10/1995 | Toda et al. |

FOREIGN PATENT DOCUMENTS

| | | |
|---|---|---|
| 0 173 516 | 3/1986 | (EP) . |
| 0 253 500 | 1/1988 | (EP) . |
| 0 253 503 | 1/1988 | (EP) . |
| WO 98/54159 | 12/1998 | (WO) . |

OTHER PUBLICATIONS

Abstract of EP 0 253 503, Jan. 20, 1988.
Abstract of EP 253 500, Nov. 14, 1989.
Abstract of EP 0 173 516, Oct. 25, 1988.
English Abstract of WO 98/54159, Dec. 10, 1998.

*Primary Examiner*—Marianne M. Cintins
*Assistant Examiner*—Vickie Kim
(74) *Attorney, Agent, or Firm*—Millen, White, Zelano, & Branigan, P.C.

(57) ABSTRACT

This invention describes the use of the compounds of general formula I

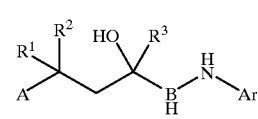

in which A, B, A, Ar, $R^1$, $R^2$ and $R^3$ have the meaning that is indicated in more detail in the description, for the production of pharmaceutical agents with anti-inflammatory action. The compounds of general formula I show a clear dissociation between anti-inflammatory and metabolic action.

26 Claims, No Drawings

NONSTEROIDAL ANTI-INFLAMMATORY AGENTS

This invention relates to the use of nonsteroidal compounds for the production of pharmaceutical agents that have an anti-inflammatory activity as well as the nonsteroidal compounds themselves.

In addition to a large number of steroid compounds, which bind well to the glucocorticoid receptor and have an anti-inflammatory action (glucocorticoids), nonsteroidal compounds are known that namely bind to the glucocorticoid receptor, for which to date no inflammatory suppression has been shown, however [cf. Nature Medicin 4 (1998) 92, Mol. Pharmacol. 52 (1997) 571]. In addition, nonsteroidal compounds were described that are derived from steroidal compounds, have an affinity to the glucocorticoid receptor and probably have an anti-inflammatory action that is mediated by the receptor [J. Med. Chem. 36, 3278–3285]. In animal experiments, however, these compounds did not show any advantages relative to steroidal glucocorticoids, i.e., it was not possible to separate the anti-inflammatory action from the metabolic effects, e.g., suppression of the suprarenal function.

Nonsteroidal compounds have now been found that bind well to the glucocorticoid receptor and, mediated by this bond, produce a suppression of inflammation. In the animal experiment, these compounds show a clear dissociation between anti-inflammatory and metabolic actions and are therefore superior both to the previously described steroidal glucocorticoids and the nonsteroidal glucocorticoids.

Compounds that are suitable according to this invention for the production of pharmaceutical agents that have an anti-inflammatory action are the nonsteroidal compounds of general formula I

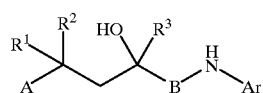

I in which $R^1$ and $R^2$ are the same or different and stand for a hydrogen atom, a $C_1$–$C_5$ alkyl group, or, together with the C-atom of the chain, stand for a ring with a total of 3–7 links, $R^3$ stands for a $C_1$–$C_5$ alkyl group or a partially or completely fluorinated $C_1$–$C_5$ alkyl group, A stands for the group

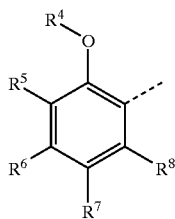

(the dashed line means the interface site), in which $R^4$ means a hydrogen atom, a $C_1$–$C_5$ alkyl group, a $C_1$–$C_{10}$ acyl group, a $C_3$–$C_{10}$ carbalkoxyalkyl group, a $C_2$–$C_5$ cyanoalkyl group, a $C_3$–$C_{10}$ unsubstituted or substituted allyl group, a $C_3$–$C_{10}$ unsubstituted or substituted propargyl group, a $C_2$–$C_5$ alkoxyalkyl group, a $C_1$–$C_5$ alkyl group that is partially or completely substituted by fluorine atoms, $R^5$ to $R^8$ are the same or different from one another and are selected from hydrogen or halogen atoms or $C_1$–$C_5$ alkoxy groups, and $R^4$ and $R^5$ together mean a heterocyclic ring, which in addition to the oxygen atom optionally can contain at least one other heteroatom from the group of oxygen, nitrogen, sulfur, with a total of 5–7 links, B stands for a carbonyl group or a $CH_2$ group, and Ar stands for a ring system, selected from the group of general partial formulas 2–5,

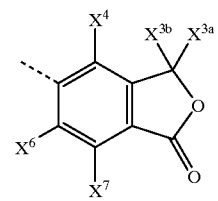

2

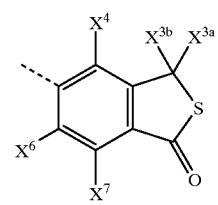

3

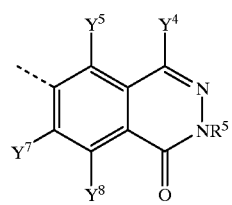

4

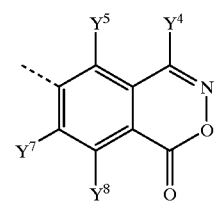

5 in which radicals $X^{3a}$, $X^{3b}$, $X^4$, $X^6$, $X^7$ (in partial formulas 2 and 3) and $Y^4$, $Y^5$, $Y^7$, and $Y^8$ (in partial formulas 4 and 5) are the same or different and are selected from hydrogen atoms, $C_1$–$C_5$ alkyl groups, partially or completely fluorinated $C_1$–$C_5$ alkyl groups, and, moreover, radicals $X^4$, $X^6$, $X^7$ (in partial formulas 2 and 3) or $Y^5$, $Y^7$, $Y^8$ (in partial formulas 4 and 5) are selected from the halogen atoms, hydroxy groups, $C_1$–$C_5$ alkoxy groups or $C_1$–$C_5$ alkanoyloxy groups, and if B stands for a $CH_2$ group, the physiologically compatible salts of the compounds of general formula I with acids.

The compounds of general formula I according to the invention can be present as different stereoisomers because of the presence of asymmetry centers. Both the racemates and the separately present stereoisomers are part of the subject of this invention.

The substituents that are defined as groups in the compounds of general formula I can have the meanings below in each case.

The $C_1$–$C_5$ alkyl groups can readily be a methyl-, ethyl-, n-propyl-, iso-propyl-, n-, iso-, or tert-butyl group or an n-pentyl, pentyl, 2,2-dimethylpropyl- or 3-methylbutyl group. A methyl or ethyl group is preferred.

A fluorine, chlorine, bromine or iodine atom can stand for a halogen atom. Fluorine, chlorine or bromine is preferred here.

If $R^1$ and $R^2$ together with the C-atom of the chain form a 3-to 7-membered ring, this is, for example, a cyclopropyl, cyclobutyl, cyclopentyl or cyclohexyl ring. The cyclopropyl ring is preferred.

For a partially or completely fluorinated $C_1$–$C_5$ alkyl group, the perfluorinated, above-mentioned alkyl groups and of the latter, mainly the trifluoromethyl group or pentafluoroethyl group, are considered, and as partially fluorinated alkyl groups, for example, the 5,5,5,4,4-pentafluoropentyl group or 5,5,5,4,4,3,3-heptafluoropentyl group is considered.

For example, a carboxymethyl, tert-butoxymethyl or ethoxymethyl group can stand for the $C_3$–$C_{10}$ carbalkoxyalkyl group; the first two mentioned groups are preferred. The information on the C-atoms relates to the C-atoms that are contained overall in the carbalkoxyalkyl group.

As representatives of the $C_2$–$C_5$ cyanoalkyl group, cyanomethyl and 1- and 2-cyanoethyl can be mentioned; cyanomethyl is preferred.

The $C_3$–$C_{10}$ allyl group is preferably an unsubstituted allyl group; in the case of a substituted allyl group, for example, 1-methylallyl, 1,1-dimethylallyl, 2-methylallyl, 3-methylallyl, 2,3-dimethylallyl, 3,3-dimethylallyl, cinnamyl and 3-cyclohexylallyl can be mentioned.

An unsubstituted propargyl, a methylpropargyl, 3-methylpropargyl, 3-phenylpropargyl or 3-cyclohexylpropargyl group are the typical representatives of a $C_3$–$C_{10}$ propargyl group; the unsubstituted propargyl group is preferred.

For example, methoxymethyl, ethoxymethyl or 2-methoxyethyl can stand for $C_2$–$C_5$ alkoxyalkyl.

Representatives of a $C_1$–$C_5$ alkoxy group are selected from methoxy, ethoxy, n-propoxy, iso-propoxy, n-butoxy, iso-butoxy, tert-butoxy or n-pentoxy, 2,2-dimethylpropoxy or 3-methylbutoxy groups. A methoxy or ethoxy group is preferred.

$C_1$–$C_5$ perfluoroalkoxy groups are the corresponding perfluorinated radicals of the $C_1$–$C_5$ alkoxy groups above.

As $C_1$–$C_5$ alkyl groups for the etherification of hydroxy groups, the above-mentioned alkyl groups are suitable; primarily a methyl or ethyl group. As a $C_1$–$C_5$ alkanoyl group for the esterification of hydroxy groups, a formyl, acetyl, propionyl, butyryl, iso-butyryl, valeryl or iso-valeryl or pivaloyl group is considered, preferably an acetyl group.

As a $C_1$–$C_{10}$ acyl group for the esterification of hydroxy groups, for example, the above-mentioned alkanoyl groups, preferably in turn an acetyl group or a benzoyl, toluoyl, phenylacetyl, acryloyl, cinnamoyl or cyclohexylcarbonyl group can be mentioned.

As a $C_1$–$C_5$ alkanoyloxy group for $X^4, X^6, X^7, Y^4, Y^5, Y^7$ or $Y^8$, a formyloxy, acetoxy, propionyloxy, butyryloxy, iso-butyryloxy, valeryloxy or iso-valeryloxy group is considered, preferably an acetoxy group.

If the compounds of general formula I (B=—CH$_2$—) are present as salts, this can be, for example, in the form of hydrochloride, sulfate, nitrate, maleate, fumarate, tartrate or benzoate.

If the compounds according to the invention are present as racemic mixtures, they can be separated into the pure, optically active forms according to the methods of racemate separation that are familiar to one skilled in the art. For example, the racemic mixtures can be separated into the pure isomers by chromatography on an even optically active carrier material (CHIRALPAK AD$^{(R)}$). It is also possible to esterify the free hydroxy group in a racemic compound of general formula I with an optically active acid and to separate the diastereoisomer esters that are obtained by fractionated crystallization or by chromatography and to saponify the separated esters in each case to the optically pure isomers. As an optically active acid, for example, mandelic acid, camphorsulfonic acid or tartaric acid can be used.

Preferred according to this invention are those compounds of general formula I, in which:

$R^1$ and $R^2$ are the same or different and stand for a hydrogen atom, a methyl or ethyl group; also together with the C-atom of the chain, $R^1$ and $R^2$ stand for a cyclopropyl ring, and/or $R^3$ stands for a $C_1$–$C_5$ perfluoroalkyl group, and/or A stands for the group

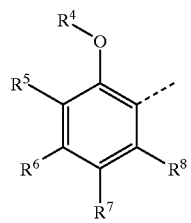

(the dashed line means the interface site), in which $R^4$ means a hydrogen atom, a methyl, ethyl, propyl or 2-propyl group, an acetyl group, a methoxy-, ethoxy- or tert-butoxycarbonyl group, a cyanomethyl group, a 2-cyanoethyl group, an allyl group, a propargyl group, a methoxymethyl-, methoxyethyl- or ethoxyethyl group, a mono-, di- or trifluoromethyl group, a pentafluoroethyl or nonafluorobutyl group, $R^5$ to $R^8$ in one or two positions mean fluorine or chlorine atoms and in the remaining positions mean hydrogen atoms, or $R^4$ and $R^5$ together with incorporation of phenyl-ring atoms 2 and 3 mean a furan, a dihydrofuran or a 2,3-dihydro-1,4-dioxine ring and $R^6, R^7$ and $R^8$ mean hydrogen atoms, $X^{3a}$ stands for a hydrogen atom or a methyl group, or $X^{3a}$ and $X^{3b}$ are the same or different and stand for a hydrogen atom or a methyl group, $X^4, X^6$ and $X^7$ are the same or different and, independently of one another, stand for a hydrogen atom or a fluorine or a chlorine atom, and/or $Y^4$ stands for a methyl, ethyl, propyl, 2-propyl or trifluoromethyl group and/or $Y^5, Y^7$ and $Y^8$ are the same or different and, independently of one another, stand for a hydrogen atom or a fluorine atom or a chlorine atom, and the other substituents all have the meanings that are indicated in formula I.

In addition, the use of those compounds of general formula I in which Ar stands for a ring system of partial formula 2 or 5 is preferred.

The use of the compounds that are mentioned below is especially preferred according to the invention:

5-{2-Hydroxy-3-[1-(2-methoxyphenyl)-cyclopropyl]-2-trifluoromethyl-propionylamino}-phthalide 5-{3-[1-(5-fluoro-2-methoxyphenyl)-cyclopropyl]-2-hydroxy-2-trifluoromethyl-propionylamino}-phthalide 5-[2-hydroxy-4-(2-methoxyphenyl)-4-methyl-2-trifluoromethyl-valeroylamino]-phthalide 5-{3-[1-(5-fluoro-2-hydoxyphenyl)-cyclopropyl]-2-hydroxy-2-trifluoromethyl-propionylamino}-phthalide 5-[4-(5-fluoro-2-hydroxyphenyl)-2-hydroxy-4-methyl-2-trifluoromethyl-valeroylamino]-phthalide 5-[4-(5-fluoro-2-hydroxyphenyl)-2-hydroxy-4-methyl-2-trifluoromethyl-pentylamino]-phthalide 4-bromo-5-[4-(5-fluoro-2-hydroxyphenyl)-2-hydroxy-4-methyl-2-trifluoromethyl-pentylamino]-phthalide 4-bromo-5-[4-(3-bromo-5-fluoro-2-hydroxyphenyl)-2-hydroxy-4-methyl-2-trifluoromethyl-pentylamino]-phthalide 6-{3-[1-(5-fluoro-2-hydroxyphenyl)-cyclopropyl]-2-hydroxy-2-trifluoromethyl-propionylamino}-4-methyl-2,3-benzoxazin-1-one 6-[4-(5-fluoro-2-methoxyphenyl)-2-hydroxy-4-methyl-2-trifluoromethyl-valeroylamino]-4-methyl-2,3-benzoxazin-1-one 6-[4-(5-fluoro-2-hydroxyphenyl)-2-hydroxy-4-methyl-2-trifluoromethyl-valeroylamino]-4-methyl-2,3-benzoxazin-1-one 6-[2-hydroxy-4-(2-hydroxyphenyl)-4-methyl-2-trifluoromethyl-valeroylamino]-4-ethyl-2,3-benzoxazin-1-one 6-[4-(5-fluoro-2-hydroxyphenyl)-2-hydroxy-4-methyl-2-trifluoromethyl-pentylamino]-4-methyl-2,3-benzoxazin-1-one 6-[4-(5-fluoro-2-hydroxyphenyl)-2-hydroxy-4-methyl-2-trifluoromethyl-pentylamino]-4-methyl-2,3-benzoxazin-1-one 6-[4-(4-bromo-2-methoxyphenyl)-2-hydroxy-4-methyl-2-trifluoromethyl-valeroylamino]-4-methyl-2,3-benzoxazin-1-one 6-[4-(4-bromo-2-methoxyphenyl)-2-hydroxy-4-methyl-2-trifluoromethyl-pentylamino]-4-methyl-2,3-benzoxazin-1-one.

In addition, the use of the compounds that are known from Tables 3–6 is preferred.

All of the above-mentioned compounds are preferably used in the form of the optical antipodes or the separate diastereomers.

Nonsteroidal compounds as such with a mixed profile that consists of gestagenic and androgenic activity in different manifestations are already the subject of PCT application PCT/EP98/03242 that was filed on Jun. 2, 1998 (priority: May 30, 1997, DE 197 23 722.3). The compounds of general formula I that are to be used according to this patent application for the production of pharmaceutical agents with anti-inflammatory action fall within the scope of the general formula that is contained in PCT application PCT/EP98/03242.

The compounds of general formula I that are cited by name below specifically fall within the scope of the general formula that is contained in the non-prepublished PCT application PCT/EP98/03242, but are not previously described by name there. They are thus novel and also meet the patenting requirement of inventive activity because of the anti-inflammatory action that is dissociated from metabolic effects and that was found for the first time in nonsteroidal compounds. These compounds as such are therefore also part of the subject of this invention.

5-{3-[1-(5-Fluoro-2-methoxyphenyl)-cyclopropyl]-2-hydroxy-2-trifluoromethyl-propionylamino}-phthalide 5-{3-[1-(5-fluoro-2-hydroxyphenyl)-cyclopropyl]-2-hydroxy-2-trifluoromethyl-propionylamino}-phthalide 4-bromo-5-[4-(5-fluoro-2-hydroxyphenyl)-2-hydroxy-4-methyl-2-trifluoromethyl-pentylamino]-phthalide 4-bromo-5-[4-(3-bromo-5-fluoro-2-hydroxyphenyl)-2-hydroxy-4-methyl-2-trifluoromethyl-pentylamino]-phthalide 6-{3-[1-(5-fluoro-2-hydroxyphenyl)-cyclopropyl]-2-hydroxy-2-trifluoromethyl-propionylamino}-4-methyl-2,3-benzoxazin-1-one 6-[2-hydroxy-4-(2-hydroxyphenyl)-4-methyl-2-trifluoromethyl-valeroylamino]-4-ethyl-2,3-benzoxazin-1-one 6-[4-(4-bromo-2-methoxyphenyl)-2-hydroxy-4-methyl-2-trifluoromethyl-pentylamino]-4-methyl-2,3-benzoxazin-1-one 5-{3-[1-(5-fluoro-2-methoxyphenyl)-cyclopropyl]-2-hydroxy-2-trifluoromethyl-propionylamino}-phthalide 6-[2-hydroxy-4-(5-fluoro-2-methoxyphenyl)-4-methyl-2-trifluoromethyl-pentylamino]-4-methyl-2,3-benzoxazin-1-one 5-{3-[1-(5-fluoro-2-hydroxyphenyl)-cyclopropyl]-2-hydroxy-2-trifluoromethyl-propionylamino}-phthalide 6-{3-[1-(5-fluoro-2-hydroxyphenyl)-cyclopropyl]-2-hydroxy-2-trifluoromethyl-propionylamino}-4-methyl-2,3-benzoxazin-1-one (−)-4-bromo-5-[4-(5-fluoro-2-hydroxyphenyl)-2-hydroxy-4-methyl-2-trifluoromethyl-pentylamino]-phthalide (−)-4-bromo-5-[4-(3-bromo-5-fluoro-2-hydroxyphenyl)-2-hydroxy-4-methyl-2-trifluoromethyl-pentylamino]-phthalide 5-[2-hydroxy-4-(5-isopropyl-2-methoxyphenyl)-4-methyl-2-trifluoromethyl-valeroylamino]-phthalide 5-[2-hydroxy-4-(2-methoxy-5-propyl-phenyl)-4-methyl-2-trifluoromethyl-valeroylamino]-phthalide 5-[2-hydroxy-4-(2-benzyloxy-5-fluorophenyl)-4-methyl-2-trifluoromethyl-valeroylamino]-phthalide 5-[2-hydroxy-4-(2-difluoromethoxy-5-fluorophenyl)-4-methyl-2-trifluoromethyl-valeroylamino]-phthalide 5-[2-hydroxy-4-(5-fluoro-2-methoxymethoxy-phenyl)-4-methyl-2-trifluoromethyl-valeroylamino]-phthalide 5-[2-hydroxy-4-(2-ethoxymethoxy-5-fluorophenyl)-4-methyl-2-trifluoromethyl-valeroylamino]-phthalide 5-{[2-hydroxy-4-[5-fluoro-2-(2-methoxyethoxy)-phenyl]-4-methyl-2-trifluoromethyl-valeroylamino}-phthalide Pharmacological Data In the glucocorticoid receptor (GR) binding test with use of cytosol preparations that consist of the thymus homogenates of rats and of [$^3$H]-dexamethasone as a reference substance, the compounds of formula I show a high to very high affinity to GR.

In addition, in the gestagen receptor binding test, these compounds show affinities for the gestagen receptor with cytosol preparations from rabbit uterus homogenates and [$^3$H]-progesterone being used as reference substances.

In addition, in the mineral corticoid receptor (MR) binding test, these compounds show affinities for MR with cytosol preparations from rat hippocampi and from [$^3$H]-aldosterone being used as reference substances.

As an essential molecular mechanism for the anti-inflammatory action of glucocorticoids, the inhibition of the transcription of cytokines, adhesion molecules, enzymes and other pro-inflammatory factors that are mediated by the GR can be seen. This inhibition is produced by an interaction of the GR with other transcription factors, e.g., AP-1 and NF-L (for a survey, see Cato, A. C. B. and Wade, E., BioEssays 18, 371–378, 1996).

The compounds of general formula I according to the invention inhibit the secretion of the cytokine IL-8 that is triggered by lipopolysaccharide (LPS) in human monocyte cell line THP-1. The concentration of the cytokines was determined in the supernatant with use of commercially available ELISA kits.

The anti-inflammatory actions of the compounds of general formula I were tested in the animal experiment by testing in the croton oil-induced inflammation in rats and mice. In this connection, croton oil in ethanolic solution was administered topically to the animals' ears. The test substances were also administered topically or systemically simultaneously with or two hours before the croton oil. After 16–24 hours, the ear weight was measured as a measurement of the inflammatory edema, the peroxidase activity was measured as a measurement for the invasions of granuloctyes, and the elastase activity was measured as a measurement for the invasions of neutrophilic granuloctyes. In this test, the compounds of general formula I inhibit the three above-mentioned inflammation parameters both after topical administration and after systemic administration.

One of the most frequent undesirable effects of a glucocorticoid therapy is the so-called "steroid diabetes" [cf. Hatz, H. J., Glucocorticoide: Immunologische Grundlagen, Pharmakologie und Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of the gluconeogenesis in the liver by induction of the enzymes that are responsible for this effect and by free amino acids, which develop from the degradation of proteins (catabolic action of glucocorticoids). A key enzyme of the catabolic metabolism in the liver is the tyrosinamino transferase (TAT). The activity of this enzyme can be determined photometrically from liver homogenates and represents a good measurement of the undesirable metabolic actions of the glucocorticoids. To measure the TAT induction, the animals are sacrificed 8 hours after the test substances are administered, the livers are removed, and the TAT activity in the homogenate is measured. In this test, at doses at which they have an anti-inflammatory action, the compounds of general formula I induce little or no tyrosinamino transferase.

Since the substances of the general formula also have a high affinity to the progesterone receptor, the new compounds were tested for their gestagenic action in the animal experiment. For this purpose, the pregnancy-maintenance test was performed on ovariectomized rats. In this respect, female rats are covered and undergo ovariectomy under anesthesia on day eight of the pregnancy two hours after substance administration. On days 8 to 14 of the pregnancy, the animals are treated daily with the test substances, and on day 15, the animals are sacrificed, and the number of living and dead fetuses per animal is determined. In the case of empty uteri, the number of implantation sites is determined by staining with 10% ammonium sulfide solution. The new compounds of formula I resulted in little or no maintenance of pregnancy up to a dose of 500 $\mu$g per kg of body weight. If the daily dose is increased to about 10 mg per kg of body weight, a weakened gestagenic action can be observed. Because of this action, the substances cannot be used as gestagens with a typical range of action.

In summary, the new compounds of general formula I compared to the previously used steroidal glucocorticoids have the following advantages:

nonsteroidal structure (i.e., the substances are also effective in patients who, because of an allergic reaction to the steroid basic structures of conventional glucocorticoids, are no longer accessible to the latter for therapy (cf. Lutz, ME, el-Azhary RA, Mayo Clin. Proc. 72, 1141–1144, 1997)

good anti-inflammatory action little metabolic action weak gestagenic action, despite the high affinity to the progesterone receptor.

Indications

Because of their anti-inflammatory and additional antiallergic, immunosuppressive and anti-proliferative actions, the compounds of general formula I according to the invention can be used as medications for treatment or prophylaxis of the following pathologic conditions in mammals and humans: In this case, the term "DISEASE" stands for the following indications:

(i) Lung diseases, which coincide with inflammatory, allergic and/or proliferative processes:

Chronically obstructive lung diseases of any origin, mainly bronchial asthma bronchitis of different origins all forms of restrictive lung diseases, mainly allergic alveolitis, all forms of pulmonary edema, mainly toxic pulmonary edema sarcoidoses and granulomatoses, especially Boeck's disease (ii) Rheumatic diseases/auto-immune diseases/degenerative joint diseases, which coincide with inflammatory, allergic and/or proliferative processes:

All forms of rheumatic diseases, especially rheumatoid arthritis, acute rheumatic fever, polymyalgia rheumatica, collagenoses reactive arthritis inflammatory soft-tissue diseases of other origins arthritic symptoms in degenerative joint diseases (arthroses)

traumatic arthritides collagen diseases of other origins, e.g., systemic lupus erythematodes, sclerodermia, polymyositis, dermatomyositis, polyarteritis nodosa, temporal arteritis Sjögren's syndrome, Still syndrome, Felty's syndrome (iii) Allergies, which coincide with inflammatory, allergic and/or proliferative processes:

All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Dermatological diseases, which coincide with inflammatory, allergic and/or proliferative processes:

Atopic dermatitis (mainly in children)

psoriasis erythematous diseases, triggered by different noxae, e.g., radiation, chemicals, burns, etc.

acid burns bullous dermatoses diseases of the lichenoid group itching (e.g., of allergic origins)

seborrheal eczema rosacea pemphigus vulgaris erythema exudativum multiforme erythema nodosum balanitis vulvitis inflammatory hair loss, such as alopecia areata cutaneous T-cell lymphoma (v) Nephropathies, which coincide with inflammatory, allergic and/or proliferative processes:

Nephrotic syndrome all nephritides (vi) Liver diseases, which coincide with inflammatory, allergic and/or proliferative processes:

Acute liver cell decomposition acute hepatitis of different origins, e.g., virally-, toxically- or pharmaceutical agent-induced chronically aggressive and/or chronically intermittent hepatitis (vii) Gastrointestinal diseases, which coincide with inflammatory, allergic and/or proliferative processes:

Regional enteritis (Crohn's disease)

ulcerative colitis gastroenteritides of other origins, e.g., native sprue (viii) Proctological diseases, which coincide with inflammatory, allergic and/or proliferative processes:

Anal eczema fissures hemorrhoids idiopathic proctitis (ix) Eve diseases, which coincide with inflammatory, allergic and/or proliferative processes:

Allergic keratitis, uveitis iritis conjunctivitis blepharitis optic neuritis chorioiditis sympathetic ophthalmia (x) Diseases of the ear-nose-throat area, which coincide with inflammatory, allergic and/or proliferative processes:

Allergic rhinitis, hay fever otitis externa, e.g., caused by contact dermatitis, infection, etc.

otitis media (xi) Neurological diseases, which coincide with inflammatory, allergic and/or proliferative processes:

Cerebral edema, mainly tumor-induced cerebral edema multiple sclerosis acute encephalomyelitis different forms of convulsions, e.g., infantile nodding spasms xii) Blood diseases, which coincide with inflammatory, allergic and/or Proliferative processes:

Acquired hemolytic anemia idiopathic thrombocytopenia (xiii) Tumor diseases, which coincide with inflammatory, allergic and/or proliferative processes:

Acute lymphatic leukemia malignant lymphoma lymphogranulomatoses lymphosarcoma extensive metastases, mainly in breast and prostate cancers (xiv) Endocrine diseases, which coincide with inflammatory, allergic and/or proliferative processes:

Endocrine orbitopathy thyrotoxic crisis de Quervain's thyroiditis

Hashimoto's thyroiditis hyperthyroidism (xv) Transplants, which coincide with inflammatory, allergic and/or proliferative processes:

(xvi) Severe shock conditions, which coincide with inflammatory, allergic and/or proliferative Processes. e.g., anaphylactic shock (xvii) Substitution therapy, which concides with inflammatory, allergic and/or proliferative processes, with:

innate primary suprarenal insufficiency, e.g., congenital adrenogenital syndrome acquired primary suprarenal insufficiency, e.g., Addison's disease, autoimmune adrenalitis, meta-infective, tumors, metastases, etc.

innate secondary suprarenal insufficiency, e.g., congenital hypopituitarism acquired secondary suprarenal insufficiency, e.g., meta-infective, tumors, etc.

(xviii) Emesis, which coincides with inflammatory, allergic and/or proliferative processes:

e.g., in combination with a 5-$HT_3$-antagonist in cytostatic-agent-induced vomiting.

The compounds of general formula I according to the invention can also be used for therapy and prophylaxis of additional pathologic conditions that are not mentioned above, for which synthetic glucocorticoids are now used (see in this connection Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xviii) are described in detail in Hatz, H. J., Glucocorticoide: Immunologische Grundlagen, Pharmakologie und Therapierichtlinien, Wissenschaftliche Verlagesgesellschaft mbH, Stuttgart, 1998.

For the therapeutic actions in the above-mentioned pathologic conditions, the suitable dose is different and it depends on, for example, the active strength of the compound of general formula I, the host, the type of administration and the type and severity of the conditions that are to be treated, as well as the use as prophylactic agent or therapeutic agent.

In addition, the invention provides (i) the use of a compound of the invention according to formula I or its mixture for the production of a medication for treating a DISEASE;

(ii) a process for treating a DISEASE, and said process comprises an administration of an amount of compound according to the invention, whereby the amount suppresses the disease and whereby the amount of compound is given to a patient who requires such a medication;

(iii) a pharmaceutical composition for treating a DISEASE, and said treatment comprises one of the compounds according to the invention or its mixture and at least one pharmaceutical adjuvant and/or vehicle.

In general, satisfactory results are to be expected in animals when the daily doses comprise a range of 1 μg to 100,000 μg of the compound according to the invention per kg of body weight. In larger mammals, for example humans, a recommended daily dose lies in the range of 1 μg to 100,000 μg per kg of body weight. Preferred is a dose of 10 to 30,000 μg per kg of body weight, more preferably a dose of 10 to 10,000 μg per kg of body weight. For example, this dose is suitably administered several times daily. For treating acute shock (e.g., anaphylactic shock), individual doses can be given that lie considerably above the above-mentioned doses.

The formulation of the pharmaceutical preparations based on the new compounds is carried out in a way that is known in the art, by the active ingredient being processed with the vehicles, fillers, substances that influence decomposition, binding agents, humectants, lubricants, absorbents, diluents, flavoring correctives, staining agents, etc. that are commonly used in galenicals and converted into the desired form of administration. In this case, reference is to be made to Remington's Pharmaceutical Science, 15th Ed. Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments, both for systemic and for local therapy.

For pulmonary administration, the new compounds can be used in the form of aerosols and inhalants.

For local application to eyes, outer ear channels, middle ear, nasal cavities, and paranasal sinuses, the new compounds can also be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%–20% in these preparations to achieve an adequate pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles. The invention also comprises a pharmaceutical composition that contains one of the pharmaceutically active compounds according to the invention or mixture thereof and a pharmaceutically compatible salt or pharmaceutically compatible adjuvant and vehicle.

In particular, the following compounds show an especially effective pharmaceutical action. In this case, the second compound is the preferred one in the group.

5-[4-(5-Fluoro-2-hydroxyphenyl)-2-hydroxy-4-methyl-2-trifluoromethyl-valeroylamino]-phthalide 5-[4-(5-fluoro-2-hydroxyphenyl)-2-hydroxy-4-methyl-2-trifluoromethyl-pentylamino]-phthalide 6-[4-(5-fluoro-2-methoxyphenyl)-2-hydroxy-4-methyl-2-trifluoromethyl-valeroylamino]-4-methyl-2,3-benzoxazin-1-one 6-[4-(4-bromo-2-methoxyphenyl)-2-hydroxy-4-methyl-2-trifluoromethyl-valeroylamino]-4-methyl-2,3-benzoxazin-1-one 6-[4-(5-fluoro-2-hydroxyphenyl)-2-hydroxy-4-methyl-2-trifluoromethyl-valeroylamino]-4-methyl-2,3-benzoxazin-1-one

EXAMPLES

The compounds of general formula I according to the invention can be produced as described below:

Production Process (1). A carbonyl compound of general formula II

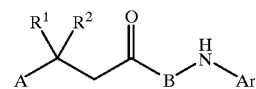

in which A, B, Ar, $R^1$ and $R^2$ have the meaning that is indicated in formula I, is reacted to a compound of formula I with a compound of general formula $C_nF_{2n+1}$—$SiR^3$, in which $R^3$ has the meaning that is indicated in general formula I, in the presence of a catalyst or with an alkyl metal compound, for example a Grignard reagent or a lithium alkyl. As a catalyst, fluoride salts or basic compounds such as alkali carbonates are suitable (J. Am. Chem. Soc. 111, 393 (1989)).

(2). A compound of general formula III

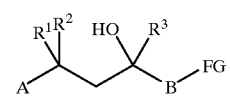

in which A, B, $R^1$, $R^2$ and $R^3$ have the meaning that is indicated in formula I and FG means a leaving group, is reacted with a compound Ar—NH—$R^9$, whereby $R^9$ means a hydrogen atom or a $C_1$–$C_5$ acyl group and Ar has the meaning that is indicated in general formula I, whereby optionally then radical $R^9$ is cleaved off to obtain a compound of formula I. In this case, the compound of general formula III can optionally be formed only as an intermediate product, e.g., it can be an acid chloride that is formed as an intermediate product from a corresponding carboxylic acid. As leaving groups, for example, a fluorine, chlorine or bromine atom or the tosylate radical can be mentioned.

(3). A compound of general formula IV

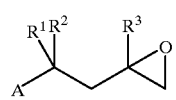

in which A, $R^1$, $R^2$ and $R^3$ have the meaning that is indicated in formula I, is reacted in a solvent or without a solvent with a compound of formula Ar—NH—$R^9$, whereby $R^9$ and Ar have the meanings that are indicated under 2, whereby optionally then radical $R^9$ is cleaved off to obtain a compound of formula I with B in the meaning of a $CH_2$ group.

(4) A compound of formula I, in which R⁴ means a hydrogen atom, is reacted with a suitable reagent to obtain compounds with radicals R⁴ in additional meanings that are indicated for formula I. Examples of this are the etherification or esterification of a corresponding hydroxyl compound.

Of the process variants above, 1. and 2. are suitable for the production of all compounds that fall under general formula I.

With the third variant, compounds of general formula I can be produced, in which B stands for a $CH_2$ group.

Optionally, compounds that were produced according to one of the above processes and in which A is an optionally substituted aromatic ring, can be substituted selectively in this aromatic radical according to known processes. Examples of this process are the catalytic hydrogenation of multiple bonds, nitration and halogenation.

The starting materials that are used in the examples are produced as follows:

Production of the Starting Materials

3-[1-(2-Methoxyphenyl)-cyclopropyl]-2-oxo-propionic acid

Corresponding to J. Org. Chem. 40 (1975) 3497, 16.7 g of 2-methoxyphenylacetonitrile, 158 ml of lithium triisopropylamide (2 molar solution) and 46.7 ml of 1,2-dichloroethane in 96 ml of tetrahydrofuran and 58.6 ml of hexamethylphosphoric acid triamide are reacted with one another. 5.6 g of 1-(2-methoxyphenyl)-cyclopropyl-carbonitrile, boiling point 104–115° C. (0.1 mbar), which is further reacted as described for 3-(1-phenyl-cyclobutyl)-2-oxo-propionic acid, is obtained. 3-[1-(2-Methoxyphenyl)-cyclopropyl]-2-oxo-propionic acid is thus obtained as an oil.

4-(5-Fluoro-2-methoxyphenyl)-2-hydroxy-4-methyl-2-trifluoromethyl-valeric acid 1.3 g of anhydrous zinc chloride and 13.2 g of granular manganese are heated to boiling in 100 ml of tetrahydrofuran and boiled with 0.2 ml of methallyl bromide for 30 minutes. Then, the solution of 25 g of methallylbromide and 17 g of trifluoropyruvic acid ethyl ester in 80 ml of tetrahydrofuran is added in drops at boiling heat over two hours and boiled for another hour. Then, it is added to saturated ammonium chloride solution and 300 ml of ethyl acetate while being cooled with ice, stirred for 30 minutes at 0° C., and the separated ethyl acetate phase is washed with saturated ammonium chloride solution and three times with water. The solvent is dried ($Na_2SO_4$) and concentrated by evaporation, and the residue is distilled in a vacuum. 17.6 g of 2-hydroxy-4-methylene-2-trifluoromethyl-valeric acid ethyl ester, boiling point 48° C., 1 hPa, is obtained.

0.8 g of anhydrous aluminum chloride is added to 5 ml of 4-fluoroanisole and 0.9 g of 2-hydroxy-4-methylene-2-trifluoromethyl-valeric acid ethyl ester. After 40 hours of stirring at room temperature, it is added to ice-cold 2N hydrochloric acid and extracted with ethyl acetate. The ethyl acetate phase is washed with 1N hydrochloric acid and water, dried ($Na_2SO_4$) and concentrated by evaporation. After chromatography on silica gel with hexane/ethyl acetate (1:1), 1 g of 4-(5-fluoro-2-methoxyphenyl)-2-hydroxy-4-methyl-2-trifluoromethyl-valeric acid ethyl ester, flash point 38–39° C., is obtained.

1.9 g of 4-(5-fluoro-2-methoxyphenyl)-2-hydroxy-4-methyl-2-trifluoromethyl-valeric acid ethyl ester is refluxed with 40 ml of potassium hydroxide in methanol (10%) for 2 hours. After the solvent is concentrated by evaporation in a vacuum, water is added, extracted with hexane, and the separated water phase is acidified with 6N hydrochloric acid. After extraction with ethyl acetate, the ethyl acetate phase is washed with water, dried ($Na_2SO_4$) and concentrated by evaporation. The residue is crystallized from hexane. 1.55 g of 4-(5-fluoro-2-methoxyphenyl)-2-hydroxy-4-methyl-2-trifluoromethyl-valeric acid, flash point 102–104° C., is obtained.

The acids of table 1 were produced analogously.

TABLE 1

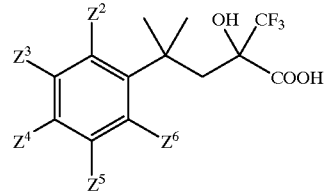

| $Z^n$ ($\neq$H) | Flash point (° C.) |
| --- | --- |
| $Z^2 = OCH_3$ | 98–99 |
| $Z^2 = Z^5 = OCH_3$ | 136–137 |
| $Z^2 = OCH_3, Z^5 = CH_3$ | 106–107 |
| $Z^2 = OCH_3, Z^4 = F$ | 103–106 |
| $Z^2 = OCH_3, Z^5 = Cl$ | 103–105 |
| $Z^2 = OCH_3, Z^4 = Br$ | 115–116 |
| $Z^2 = OCH_3, Z^5 = C_3H_7$ | 106 |
| $Z^2 = OCH_3, Z^5 = CH(CH_3)_2$ | 137–138 |

By conversion according to standard processes, additional acids are obtained from the acids above or from their precursors:

4-(4-Cyano-2-methoxyphenyl)-2-hydroxy-4-methyl-2-trifluoromethyl-valeric acid

The title compound is obtained from 4-(4-bromo-2-methoxyphenyl)-2-hydroxy-4-methyl-2-trifluoromethyl-valeric acid ethyl ester, zinc cyanide and tetrakis-triphenylphosphine-palladium in dimethylformamide at 140° C. After saponification, the title acid is obtained as an amorphous powder.

4-(4-Iodo-2-methoxyphenyl)-4-methyl-2-oxo-valeric acid 3.2 g of 4-iodo-2-methoxybenzoic acid-methyl ester in 10 ml of diethyl ether is added to 24.2 mmol of methylmagnesium bromide in 23 ml of diethyl ether. After 20 hours, ammonium chloride solution is added, the ether phase is separated, dried and concentrated by evaporation. 2.4 g of the residue is dissolved in 10 ml of dichloromethane, mixed with 714 mg of 2-trimethylsilyloxy-acrylic acid-ethyl ester, cooled to −70° C. and mixed with 0.27 ml of tin(IV) chloride. After 15 minutes, the solution is added to potassium carbonate solution. After extraction with diethyl ether, the organic phase is washed with water, dried and concentrated by evaporation. 500 mg of the 4-(4-iodo-2-methoxyphenyl)-4-methyl-2-oxo-valeric acid ethyl ester that is thus obtained is stirred with 8.6 ml of 1 M sodium hydroxide in ethanol/water (2:1, v/v) for 3 hours at room temperature. After water is added, it is extracted with diethyl ether, the water phase is acidified with 1 m hydrochloric acid and extracted with diethyl ether. After drying and concentration by evaporation, 410 mg of 4-(4-iodo-2- methoxyphenyl)-4-methyl-2-oxo-valeric acid is obtained as a yellowish oil.

4-(5-Fluoro-2-methoxyphenyl)-4-methyl-2-oxo-valeric acid is obtained analogously to the embodiment above, flash point 58–60° C.

4-(4-Bromo-2-methoxyphenyl)-2-oxo-valeric acid is obtained analogously to the embodiment above as an oil.

4-(2,3-Dihydro-7-benzofuranyl)-4-methyl-2-oxo-valeric acid 1.69 g of 1-(2,3-dihydro-7-benzofuranyl)-1-methyl-ethanol is obtained in the usual way from 1.7 g of 2,3-dihydro-benzofuran-7-carboxylic acid methyl ester in 35 ml of diethyl ether and 7 ml of a 3 molar solution of methyl-magnesium chloride in tetrahydrofuran. This product is reacted analogously to the process that is described for 4-(4-iodo-2-methoxyphenyl)-4-methyl-2-oxo-valeric acid. 1.8 g of the title compound is obtained as a yellow-brown oil.

4-(3-Chloro-2-methoxyphenyl)-2-oxo-valeric acid 8.2 ml of methyl iodide is added to 10 g of 3-chlorosalicylic acid and 18 g of potassium carbonate in 88 ml of dimethylformamide, and the mixture is stirred overnight. It is diluted with water, extracted with ethyl acetate, the organic phase is dried ($Na_2SO_4$) and concentrated by evaporation. The residue is distilled on a bulb tube. 10 g of 3-chloro-2-methoxybenzoic acid methyl ester is obtained, boiling point 100° C./0.17 mbar.

This ester is reacted analogously to the process that is described for 4-(4-iodo-2-methoxyphenyl)-4-methyl-2-oxo-valeric acid. 8 g of the title compound is obtained as a light yellow oil.

4-(6-Fluoro-2-methoxyphenyl)-2-oxo-valeric acid 18 g of the title compound is obtained as a light yellow oil from 18 g of 6-fluorosalicylic acid analogously to the process that is described for 4-(3-chloro-2-methoxyphenyl)-2-oxo-valeric acid.

4-Toluenesulfonic acid-[4-(5-fluoro-2-methoxyphenyl)-2-hydroxy-4-methyl-2-trifluoromethyl-pentyl)-ester 810 mg of 4-(5-fluoro-2-methoxyphenyl)-2-hydroxy-4-methyl-2-trifluoromethyl-valeric acid is reduced in 20 ml of ether with 190 mg of lithium-aluminum hydride. After aqueous sodium bicarbonate solution is added, the ether phase is separated, dried ($Na_2SO_4$), concentrated by evaporation, and the residue is distilled on a bulb tube. 700 mg of 2-hydroxy-4-(5-fluoro-2-methoxyphenyl)-4-methyl-2-trifluoromethyl-pentanol, which is dissolved in 7 ml of pyridine and is mixed at 0° C. with 440 mg of 4-toluenesulfonic acid chloride, is obtained. After 2 days at 0° C., it is concentrated by evaporation in a vacuum, dispersed between 1 M hydrochloric acid and ethyl acetate, the ethyl acetate phase is washed several times with 1 M hydrochloric acid, dried ($Na_2SO_4$) and concentrated by evaporation. The title compound is thus obtained, flash point 93–94° C.

4-Toluenesulfonic acid-[4-(5-fluoro-2-methoxyphenyl)-2-hydroxy-2-trifluoromethyl-pentyl]-ester is produced analogously to the previous instructions, flash point 48–50° C.

2-[2-(5-Fluoro-2-methoxyphenyl)-2-methyl-propyl]-2-trifluoromethyl-oxiran 3.5 g of 2-hydroxy-4-(5-fluoro-2-methoxyphenyl)-4-methyl-2-trifluoromethyl-pentanol and 3.45 g of triphenylphosphine are dissolved in 50 ml of tetrahydrofuran and mixed in 3 portions at 0° C. with 2.5 ml of azodicarboxylic acid-diethyl ester. After one hour at 0° C., it is stirred for 16 more hours at room temperature, then refluxed for 7 hours and again stirred for 48 hours at room temperature. After concentration by evaporation, a hexane-isopropylether mixture is added, filtered, and the filtrate is chromatographed on silica gel. The product that is eluted with hexane/ethyl acetate is distilled on a bulb tube, boiling point 100° C./0.5 mbar.

2-[2-(4-Bromo-2-methoxyphenyl)-2-methyl-propyl]-2-trifluoromethyl-oxiran is obtained analogously to the example above, boiling point 120° C./0.04 mbar.

4-Bromo-5-aminophthalide 23 g of 3-bromo-4-nitro-1,2-xylene is suspended in 200 ml of pyridine and 600 ml of water and mixed at 60° C. in portions with 260 g of potassium permanganate, whereby the temperature increases to 90° C. It is heated for 2 more hours to 95° C., filtered, the filtrate is acidified with hydrochloric acid and extracted with diethyl ether. After concentration by evaporation of the solvent, 27 g of 3-bromo-4-nitrophthalic acid is obtained.

12 g of the acid is heated for 15 minutes to 220° C., and then it is distilled on a bulb tube. At 0.03 hPa, 10 g of 3-bromo-4-nitrophthalic acid anhydride is distilled.

The anhydride is dissolved in 120 ml of dimethylformamide and slowly mixed at 0° C. with 78.8 ml of a 0.5 M solution of sodium borohydride in dimethylformamide. After three hours at 0° C., 2N hydrochloric acid is carefully added and extracted with ethyl acetate. After washing with potassium bicarbonate solution, drying ($Na_2SO_4$) and concentration by evaporation of the ethyl acetate phase, 6.6 g of 4-bromo-5-nitrophthalide is obtained.

6.6 g of 4-bromo-5-nitrophthalide is dissolved in 45 ml of ethanol and added in drops to a mixture of 65 g of iron(II) sulfate, 220 ml of water and 65 ml of ammonia (33%) that is heated to 60° C. and thoroughly stirred. After 2 hours at 60° C., the mixture is absorptively precipitated five times with 200 ml of diethyl ether. The diethyl ether phases are concentrated by evaporation. As a residue, 4.1 g of 4-bromo-5-aminophthalide is obtained, flash point 176–180° C.

6-Bromo-5-aminophthalide

4-Bromo-5-nitrophthalic acid anhydride is produced analogously to the above-described process from 4-bromo-5-nitro-1,2-xylene.

By boiling with ethanol, a mixture of 2-bromo-6-ethoxycarbonyl-3-nitro-benzoic acid and 3-bromo-2-ethoxycarbonyl-4-nitro-benzoic acid is obtained from the above.

1.2 ml of oxalyl chloride is carefully added in drops at 0° C. to 7.2 ml of a 0.66 m solution of dimethylformamide in dichloromethane. The solution is stirred for 1 hour at 0° C. and for 5 minutes at room temperature. After concentration by evaporation in a vacuum, the residue is suspended in 7 ml of acetonitrile, cooled to −35° C. and mixed drop by drop with 1.5 g of the ester mixture. After one hour at the same temperature, it is cooled to −70° C., and 2.4 ml of a 2 m solution of sodium borohydride in dimethylformamide is added in drops. It is stirred for 20 hours at room temperature, water is added, alkalized with potassium carbonate and extracted with diethyl ether. The diethyl ether phase is dried (Na$_2$SO$_4$) and concentrated by evaporation. A mixture of 5-bromo-6-nitrophthalide and 6-bromo-5-nitrophthalide, which is separated on silica gel with hexane/ethyl acetate (95:5) is obtained.

The reduction to aminophthalide is carried out as described above. 6-Bromo-5-aminophthalide is obtained, flash point 235–241° C.

The phthalides of Table 2 are obtained analogously.

TABLE 2

| X$^{3a}$/X$^{3b}$ | Flash point [° C.] |
|---|---|
| CH$_3$/H | 152–156 |
| CH$_3$/CH$_3$ | 94–97 |
| C$_2$H$_5$/H | 137–140 |
| C$_2$H$_5$/C$_2$H$_5$ | 95–96 |

5-Acetamido-phthalide 3 g of 5-amino-phthalide, 10 ml of acetic anhydride and 30 ml of tetrahydrofuran are refluxed for 1 hour. The crystals that are precipitated after cooling are suctioned off and washed with isopropylether. 3.3 g of the title compound is obtained, flash point >300° C.

6-Amino-4-methyl-2,3-benzoxazin-1-one 60 g of 2-methyl-5-nitroacetophenone, 38.5 g of 2,2-dimethyl-1,3-propanediol and 6 g of p-toluenesulfonic acid are boiled in 1 l of toluene with a water separator until water is no longer produced. The solution is washed with potassium bicarbonate, dried (Na$_2$SO$_4$) and concentrated by evaporation. 71.7 g of the crystalline ketal is obtained from pentane.

The latter is oxidized in 1.5 ml of pyridine and 4.5 of water with 350 g of potassium permanganate, as described above in the production of 4-bromo-5-aminophthalide. 56.4 g of 4-nitro-2-(2,5,5-trimethyl-1,3-dioxan-2-yl)-benzoic acid is obtained.

52 g of the acid is hydrogenated in 500 ml of methanol and 500 ml of ethyl acetate with 10 g of palladium/carbon (10%). 45.5 g of the crystalline amino compound is obtained from pentane.

10 g of the amine is refluxed with 100 ml of concentrated hydrochloric acid for 2 hours. The solvent is concentrated by evaporation in a vacuum, and the residue is refluxed with 15.7 g of hydroxylamine hydrochloride, 8.4 g of potassium hydroxide, 120 ml of ethanol and 50 ml of water for 12 hours. It is diluted with water, and the crystals are suctioned off. After drying, 3.5 g of 6-amino-4-methyl-2,3-benzoxazin-1-one is obtained, flash point 291–296° C.

6-Amino-4-ethyl-2,3-benzoxazin-1-one is obtained analogously from 2-methyl-5-nitropropiophenone, flash point 89–93° C.

6-Acetamido-4-methyl-2,3-benzoxazin-1-one

This compound is obtained analogously to the 5-acetamido-phthalide from 6-amino-4-methyl-2,3-benzoxazin-1-one, refluxed only for 6 days and then water is added and extracted with ethyl acetate. After drying and concentration by evaporation of the solvent, the title compound is obtained as crystals, flash point 223–229° C.

5-[4-(4-Iodo-2-methoxyphenyl)-4-methyl-2-oxo-valeroylamino)-phthalide 1.7 g of 4-(4-iodo-2-methoxyphenyl)-4-methyl-2-oxo-valeric acid is dissolved in 25 ml of dimethyl acetamide and mixed under argon at −8° C. with 0.37 ml of thionyl chloride. After 20 minutes of stirring at −3 to +3° C., 700 mg of 5-aminophthalide is added. It is stirred for 1.5 hours at room temperature, then mixed with water, extracted with ethyl acetate, the organic phase is washed with water, dried (Na$_2$SO$_4$), and after the solvent is concentrated by evaporation and after chromatography of the crude product on silica gel with hexane/ethyl acetate (80:20), 1.5 g of 5-[4-(4-iodo-2-methoxyphenyl)-4-methyl-2-oxo-valeroylamino)-phthalide is obtained as a foam.

5-[4-(4-Bromo-2-methoxyphenyl)-4-methyl-2-oxo-valeroylamino)-phthalide was obtained from 5-aminophthalide and 4-(4-bromo-2-methoxyphenyl)-4-methyl-2-oxo-valeric acid analogously to the process that is described for 5-[4-(4-iodo-2-methoxyphenyl)-4-methyl-2-oxo-valeroylamino)-phthalide, flash point 136–140° C.

5-[4-(3-Chloro-2-methoxyphenyl)-4-methyl-2-oxo-valeroylamino)-phthalide was obtained as a beige-colored foam from 5-aminophthalide and 4-(3-chloro-2-methoxyphenyl)-4-methyl-2-oxo-valeric acid analogously to the process that is described for 5-[4-(4-iodo-2-methoxyphenyl)-4-methyl-2-oxo-valeroylamino]-phthalide.

5-[4-(6-Fluoro-2-methoxyphenyl)-4-methyl-2-oxo-valeroylamino)-phthalide was obtained from 5-aminophthalide and 4-(6-fluoro-2-methoxyphenyl)-4-methyl-2-oxo-valeric acid analogously to the process that is described for 5-[4-(4-iodo-2-methoxyphenyl)-4-methyl-2-oxo-valeroylamino)-phthalide, flash point 175–179° C.

5-{3-[1-(2-Methoxyphenyl)-cyclopropyl]-2-oxo-propionylamino}-phthalide was obtained from 5-aminophthalide and 3-[1-(2-methoxyphenyl)-cyclopropyl]-2-oxo-propionic acid analogously to the process that is described for 5-[4-(4-iodo-2-methoxyphenyl)-4-methyl-2-oxo-valeroylamino)-phthalide, flash point 190–202° C.

5-{3-[1-(5-Fluoro-2-methoxyphenyl)-cyclopropyl]-2-oxo-propionylamino}-phthalide was obtained from 5-aminophthalide and 3-[1-(5-fluoro-2-methoxyphenyl)-cyclopropyl]-2-oxo-propionic acid analogously to the process that is described for 5-[4-(4-iodo-2-methoxyphenyl)-4-methyl-2-oxo-valeroylamino)-phthalide, flash point 190–193° C.

5-[4-(2,3-Dihydro-7-benzofuranyl)-4-methyl-2-oxo-valeroylamino]-phthalide was obtained as a white foam from 5-aminophthalide and 4-(2,3-dihydro-7-benzofuranyl)-4-methyl-2-oxo-valeric acid analogously to the process that is described for 5-[4-(4-iodo-2-methoxyphenyl)-4-methyl-2-oxo-valeroylamino]-phthalide.

6-[4-(5-Fluoro-2-methoxyphenyl)-4-methyl-2-oxo-valeroylamino]-4-methyl-2,3-benzoxazin-1-one was obtained from 6-amino-4-methyl-2,3-benzoxazin-1-one and 4-(5-fluoro-2-methoxyphenyl)-4-methyl-2-oxo-valeric acid analogously to the process that is described for 5-[4-(4-iodo-2-methoxyphenyl)-4-methyl-2-oxo-valeroylamino)-phthalide, flash point 171–173° C.

4-Ethyl-6-[4-(5-fluoro-2-methoxyphenyl)-4-methyl-2-oxo-valeroylamino)-2,3-benzoxazin-1-one was obtained from 6-amino-4-ethyl-2,3-benzoxazin-1-one and 4-(5-fluoro-2-methoxyphenyl)-4-methyl-2-oxo-valeric acid analogously to the process that is described for 5-[4-(4-iodo-2-methoxyphenyl)-4-methyl-2-oxo-valeroylamino)-phthalide, flash point 157–158° C.

6-[4-(6-Fluoro-2-methoxyphenyl)-4-methyl-2-oxo-valeroylamino]-4-methyl-2,3-benzoxazin-1-one was obtained from 6-amino-4-methyl-2,3-benzoxazin-1-one and 4-(6-fluoro-2-methoxyphenyl)-4-methyl-2-oxo-valeric acid analogously to the process that is described for 5-[4-(4-iodo-2-methoxyphenyl)-4-methyl-2-oxo-valeroylamino)-phthalide, flash point 178–181° C.

6-[1-(5-Fluoro-2-methoxyphenyl)-cyclopropyl)-2-oxo-propionylamino]-4-methyl-2,3-benzoxazin-1-one was obtained from 6-amino-4-methyl-2,3-benzoxazin-1-one and 3-[1-(5-fluoro-2-methoxyphenyl)-cyclopropyl]-2-oxo-propionic acid analogously to the process that is described for 5-[4-(4-iodo-2-methoxyphenyl)-4-methyl-2-oxo-valeroylamino)-phthalide, flash point 222–227° C.

6-[4-(2,3-Dihydro-7-benzofuranyl)-4-methyl-2-oxo-valeroylamino]-4-methyl-2,3-benzoxazin-1-one was obtained from 6-amino-4-methyl-2,3-benzoxazin-1-one and 4-(2,3-dihydro-7-benzofuranyl)-4-methyl-2-oxo-valeric acid analogously to the process that is described for 5-[4-(4-iodo-2-methoxyphenyl)-4-methyl-2-oxo-valeroylamino)-phthalide, flash point 171–177° C.

The examples below are used for a more detailed explanation of the invention. Additional compounds can be produced by using homologous/analogous reagents. The necessary starting compounds are described above under "Starting Compounds."

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 19856475.9 filed Nov. 27, 1998, is hereby incorporated by reference.

Example 1

Process 1

5-{2-Hydroxy-3-[1-(2-methoxyphenyl)-cyclopropyl]-2-trifluoromethyl-propionylamino}-phthalide 500 mg of 5-{3-[1-(2-methoxyphenyl)-cyclopropyl]-2-oxo-propionylamino}-phthalide is dissolved under argon in 15 ml of dimethylformamide and mixed with 0.77 ml of trifluoromethyl-trimethylsilane and 500 mg of cesium carbonate while being cooled with ice. After 18 hours of stirring at room temperature, 5 ml of a 1 M solution of tetrabutylammonium fluoride in tetrahydrofuran and a few drops of water are added and stirred for one hour at room temperature. After 100 ml of water is added, it is extracted with ethyl acetate, the organic phase is dried ($Na_2SO_4$) and concentrated by evaporation. The crude product is chromatographed on silica gel. With hexane/ethyl acetate (80:20), the title compound is obtained in a pure state.

The enantiomer mixture is separated by chromatography on chiral support medium (CHIRALPAK AD$^{(R)}$, DAICEL Company) with hexane/2-propanol/ethanol (900:25:25, vvv).

(+)-Enantiomer with flash point 200–208° C., $[\alpha]_D$+106.9°·(c=0.5, $CHCl_3$), (−)-enantiomer with flash point 195–208° C., $[\alpha]_D$−104.9°·(c=0.5, $CHCl_3$) are thus obtained.

Example 2

5-{3-[1-(5-Fluoro-2-methoxyphenyl)-cyclopropyl]-2-hydroxy-2-trifluoromethyl-propionylamino}-phthalide is obtained from 5-{3-[1-(5-fluoro-2-methoxyphenyl)-cyclopropyl]-2-oxo-propionylamino}-phthalide analogously to Example 1. Flash point 170–179° C. (racemate).

Example 3

Process 2

5-[2-Hydroxy-4-(2-methoxyphenyl)-4-methyl-2-trifluoromethyl-valeroylamino]-phthalide 400 mg of 2-hydroxy-4-(2-methoxyphenyl)-4-methyl-2-trifluoromethyl-valeric acid is mixed in 5 ml of dimethylacetamide at 0° C. with 0.23 ml of thionyl chloride. After 30 minutes of stirring at 0° C., 390 mg of 5-aminophthalide in 2 ml of dimethylacetamide is added, and the mixture is stirred for another 4 hours at this temperature. Then, ice water is added, extracted with ethyl acetate, and after drying ($Na_2SO_4$), the crude product is chromatographed on silica gel. With hexane/ethyl acetate (50:50), the title compound is obtained in a crystalline state, flash point 134–135° C.

After racemate separation, (+)-Enantiomer with flash point 135–136° C., $[\alpha]_D$+192.2°·(c=1, $CHCl_3$), (−)-enantiomer with flash point 136–137° C., $[\alpha]_D$−194.8°·(c=1, $CHCl_3$) are obtained.

The compounds of Table 3 are obtained analogously.

TABLE 3

[Structure: phenyl ring with $Z^2, Z^3, Z^4, Z^5, Z^6$ substituents, connected via C(CH$_3$)$_2$–CH$_2$–C(OH)(CF$_3$)–C(=O)–NH– to a 5-substituted phthalide (isobenzofuran-1(3H)-one)]

| Example | $Z^n$ (≠H) | Flash Point (° C.) | Isomerism or $[\square]_D$ (c = 0.5) (1) |
|---|---|---|---|
| 4 | $Z^2 = Z^5 = OCH_3$ | 145 | racemate |
| 5 | $Z^2 = OCH_3, Z^5 = CH_3$ | 126–127 | racemate |
| 6 | $Z^2 = OCH_3, Z^5 = CH_3$ | 169–170 | (+)-form |
| 7 | $Z^2 = OCH_3, Z^5 = CH_3$ | 169 | (−)-form |
| 8 | $Z^2 = OCH_3, Z^5 = CH(CH_3)_2$ | 135 | racemate |
| 9 | $Z^2 = OCH_3, Z^5 = C_3H_7$ | 120–122 | racemate |
| 10 | $Z^2 = OCH_3, Z^4 = F$ | 180–181 | racemate |
| 11 | $Z^2 = OCH_3, Z^5 = F$ | 140–141 | racemate |
| 12 | $Z^2 = OCH_3, Z^6 = F$ | 171–174 | racemate |
| 13 | $Z^2 = OCH_3, Z^3 = Cl$ | 72–74 | racemate |
| 14 | $Z^2 = OCH_3, Z^5 = Cl$ | 141 | racemate |
| 15 | $Z^2 = OCH_3, Z^5 = Cl$ | 106–108 | +105.5 (1) |
| 16 | $Z^2 = OCH_3, Z^5 = Cl$ | 105–207 | −97 (1) |
| 17 | $Z^2 = OCH_3, Z^4 = Br$ | 144–145 | racemate |
| 18 | $Z^2 = OCH_3, Z^4 = Br$ | 176–177 | (+)-enantiomer |
| 19 | $Z^2 = OCH_3, Z^4 = Br$ | 177–178 | −139.6 |
| 20 | $Z^2 = OCH_3, Z^4 = I$ | 175–180 | racemate |
| 21 | $Z^2 = OCH_3, Z^4 = Cn$ | 135–136 | racemate |

(1) The optically active compounds that are presented in the table were separated analogously to Example 1. Unless otherwise indicated, the measurement was made in methanol.

If 6-amino-4-methyl-2,3-benzoxazin-1-one or 6-amino-4-ethyl-2,3-benzoxazin-1-one is used in Example 3 instead of 5-aminophthalide, the examples that are listed in Table 4 are obtained.

TABLE 4

[Structure: phenyl ring with $Z^2, Z^3, Z^4, Z^5, Z^6$ substituents, connected via C(CH$_3$)$_2$–CH$_2$–C(OH)(CF$_3$)–C(=O)–NH– to a 4-$Y^4$-substituted 2,3-benzoxazin-1-one]

| Example | $Z^n$ (≠H) | $Y^4$ | Flash Point (° C.) | Isomerism or $[\square]_D$ (c = 0.5) (1) |
|---|---|---|---|---|
| 22 | $Z^2 = OCH_3$ | $CH_3$ | 161–163 | Racemate |
| 23 | $Z^2 = OCH_3$ | $CH_3$ | 173–175 | −54.7 |
| 24 | $Z^2 = OCH_3$ | $CH_3$ | 173–175 | +52.2 |
| 25 | $Z^2 = OCH_3$ | $C_2H_5$ | 164 | racemate |
| 26 | $Z^2 = OCH_3$ | $C_2H_5$ | 190–191 | (+)-form |
| 27 | $Z^2 = OCH_3$ | $C_2H_5$ | 190–191 | −161.3 (CHCl$_3$) |
| 28 | $Z^2 = OCH_3, Z^5 = CH_3$ | $CH_3$ | 166–167 | racemate |
| 29 | $Z^2 = OCH_3, Z^5 = F$ | $CH_3$ | 165 | racemate |
| 30 | $Z = OCH_3, Z^5 = F$ | $CH_3$ | 188–189 | (+)-form |
| 31 | $Z^2 = OCH_3, Z^5 = F$ | $CH_3$ | 187–188 | −132.8 (CHCl$_3$) |

TABLE 4-continued

| Example | $Z^n$ (≠H) | $Y^4$ | Flash Point (° C.) | Isomerism or $[\square]_D$ (c = 0.5) (1) |
|---|---|---|---|---|
| 32 | $Z^2 = OCH_3, Z^5 = F$ | $C_2H_5$ | 126–128 | racemate |
| 33 | $Z^2 = OCH_3, Z^5 = F$ | $C_2H_5$ | 170–171 | −147.4 |
| 34 | $Z^2 = OCH_3, Z^5 = F$ | $C_2H_5$ | 171 | (+)-form |
| 35 | $Z^2 = OCH_3, Z^6 = F$ | $CH_3$ | 209–219 | racemate |
| 36 | $Z^2 = OCH_3, Z^5 = Cl$ | $CH_3$ | 182–184 | racemate |
| 37 | $Z^2 = OCH_3, Z^5 = Cl$ | $CH_3$ | 198–199 | +90.0 |
| 38 | $Z^2 = OCH_3, Z^5 = Cl$ | $CH_3$ | 197–198 | −90.2 |
| 39 | $Z^2 = OCH_3, Z^4 = Br$ | $CH_3$ | 206–207 | racemate |
| 40 | $Z^2 = OCH_3, Z^4 = Br$ | $CH_3$ | 194–198 | (+)-form |
| 41 | $Z^2 = OCH_3, Z^4 = Br$ | $CH_3$ | 196–198 | −122.2 (CHCl$_3$) |

(1) The optically active compounds that are presented in the table were separated analogously to Example 1. Unless otherwise indicated, the measurement was made in methanol.

Example 42

5-[2-Hydroxy-4-(5-fluoro-2-methoxyphenyl)-4-methyl-2-methyl-pentylamino]-phthalide 688 mg of 5-acetamidophthalide in 15 ml of dimethylformamide is mixed under argon at 0° C. with 108 mg of an 80% sodium hydride/oil suspension. After 10 minutes of stirring at this temperature, 556 mg of 4-toluenesulfonic acid-[2-hydroxy-4-(5-fluoro-2-methoxyphenyl)-2-trifluoromethyl-pentyl]-ester is added. After 16 hours of stirring at 60° C., it is added to 1 M hydrochloric acid, neutralized with potassium carbonate and extracted with ethyl acetate. After drying (Na$_2$SO$_4$), the crude product is chromatographed on silica gel. With hexane/ethyl acetate (60:40), the title compound is obtained in a crystalline state, flash point 148–149° C.

Example 43

6-[2-Hydroxy-4-(5-fluoro-2-methoxyphenyl)-4-methyl-2-trifluoromethyl-pentylamino]-4-methyl-2,3-benzoxazin-1-one 584 mg of 2-[2-(5-fluoro-2-methoxyphenyl)-2-methyl-propyl]-2-trifluoromethyl-oxiran, 282 mg of 6-amino-4-methyl-2,3-benzoxazin-1-one and 1 ml of 1,3-dimethyl-3,4,5,6-tetrahydro-2[1H]-pyrimidinone are heated to 120° C. for 6 hours. After 1 ml of tetrahydrofuran is added, it is chromatographed on silica gel, and the title compound is eluted with hexane/ethyl acetate/tetrahydrofuran (55:40:5), flash point 178–179° C.

Example 44

5-{3-[1-(5-Fluoro-2-hydroxyphenyl)-cyclopropyl]-2-hydroxy-2-trifluoromethyl-propionylamino}-phthalide 225 mg of 5-{3-[1-(5-fluoro-2-methoxyphenyl)-cyclopropyl]-2-hydroxy-2-trifluoromethyl-propionylamino}-phthalide is mixed in 4.5 ml of dichloromethane at 0° C. with 2.48 ml of a 1 molar solution of boron tribromide in dichloromethane. After 3 hours of stirring at 0° C., the mixture is added to water, extracted with ethyl acetate, the organic phase is dried ($Na_2SO_4$) and concentrated by evaporation. After the residue is triturated with hexane, the title compound is obtained in crystalline form, flash point 196–199° C.

Example 45

6-{3-[1-(5-Fluoro-2-hydroxyphenyl)-cyclopropyl]-2-hydroxy-2-trifluoromethyl-propionylamino}-4-methyl-2,3-benzoxazin-1-one is obtained from 6-{3-[1-(5-fluoro-2-methoxyphenyl)-cyclopropyl]-2-hydroxy-2-trifluoromethyl-propionylamino}-4-methyl-2,3-benzoxazin-1-one analogously to 5-{3-[1-(5-fluoro-2-hydroxyphenyl)-cyclopropyl]-2-hydroxy-2-trifluoromethyl-propionylamino}-phthalide, flash point 236–244° C.

Example 46

6-[2-Hydroxy-4-(5-fluoro-2-hydroxyphenyl)-4-methyl-2-trifluoromethyl-valeroylamino]-4-methyl-2,3-benzoxazin-1-one is obtained from 6-[2-hydroxy-4-(5-fluoro-2-methoxyphenyl)-4-methyl-2-trifluoromethyl-valeroylamino]-4-methyl-2,3-benzoxazin-1-one analogously to 5-{3-[1-(5-fluoro-2-hydroxyphenyl)-cyclopropyl]-2-hydroxy-2-trifluoromethyl-propionylamino}-phthalide, flash point 234–236° C., (+)-Enantiomer, flash point 230–234° C., $[\alpha]_D$ +34°·(c=0.5)

(−)-enantiomer, flash point 230–232° C., $[\alpha]_D$ −34.1°·(C=0.5).

Example 47

6-[2-Hydroxy-4-(2-hydroxyphenyl)-4-methyl-2-trifluoromethyl-valeroylamino]-4-ethyl-2,3-benzoxazin-1-one is obtained from 6-[2-hydroxy-4-(2-methoxyphenyl)-4-methyl-2-trifluoromethyl-valeroylamino]-4-ethyl-2,3-benzoxazin-1-one analogously to 5-{3-[1-(5-fluoro-2-hydroxyphenyl)-cyclopropyl]-2-hydroxy-2-trifluoromethyl-propionylamino}-phthalide, flash point 164° C.

(+)-Enantiomer with flash point 191–192° C., $[\alpha]_D$ +161.5°·(c=0.5, $CHCl_3$)

(−)-enantiomer with flash point 190–191° C., $[\alpha]_D$ −161.3°·(c=0.5, $CHCl_3$)

The examples of Tables 5A and 5B are obtained analogously.

TABLE 5A

| Example | B | $Z^n$ (≠H) | Flash Point (° C.) | Isomerism or $[\square]_D$ (c = 0.5) (1) |
|---|---|---|---|---|
| 48 | C=O | $Z^2$ = OH | 222–224 | racemate |
| 49 | C=O | $Z^2$ = $Z^5$ = OH | 265–267 | racemate |
| 50 | C=O | $Z^2$ = OH, $Z^5$ = $CH_3$ | 215–217 | racemate |
| 51A | C=O | $Z^2$ = OH, $Z^5$ = $CH_3$ | 173–174 | (+)-form |
| 52 | C=O | $Z^2$ = OH, $Z^5$ = $CH_3$ | 174–175 | (−)-form |
| 53 | C=O | $Z^2$ = OH, $Z^5$ = $CH(CH_3)_2$ | 163–165 | racemate |
| 51B | C=O | $Z^2$ = OH, $Z^5$ = $C_3H_7$ | 162 | racemate |
| 54 | C=O | $Z^2$ = OH, $Z^4$ = F | 240–242 | racemate |
| 55 | C=O | $Z^2$ = OH, $Z^5$ = F | 207–211 | +166° ($CHCl_3$) |
| 56 | C=O | $Z^2$ = OH, $Z^5$ = F | 207–211 | −165.8° ($CHCl_3$) |
| 57 | C=O | $Z^2$ = OH, $Z^6$ = F | 215–225 | racemate |
| 58 | C=O | $Z^2$ = OH, $Z^5$ = Cl | 220–221 | racemate |
| 59 | C=O | $Z^2$ = OH, $Z^5$ = Cl | >100° C. decomposition | (+)-enantiomer |
| 60 | C=O | $Z^2$ = OH, $Z^4$ = Br | 224–226 | racemate |
| 61 | $CH_2$ | $Z^2$ = OH, $Z^5$ = F | 156–157 | racemate |
| 62 | $CH_2$ | $Z^2$ = OH, $Z^5$ = F | 157–159 | +23.5 |
| 63 | $CH_2$ | $Z^2$ = OH, $Z^5$ = F | 157–159 | −18.7 |
| 64 | C=O | $Z^2$ = OH, $Z^4$ = Br | 224–226 | racemate |

(1) The optically active compounds that are presented in the table were separated analogously to Example 1. Unless otherwise indicated, the measurement was made in methanol:

TABLE 5B

| Example | B | $Z_n$ (≠H) | Flash Point (° C.) | Isomerism or $[\square]_D$ (c = 0.5) (1) |
|---|---|---|---|---|
| 65 | C=O | $Z^2$ = OH, $Z^5$ = F | 234–236 | racemate |
| 66 | C=O | $Z^2$ = OH, $Z^5$ = F | 232–234 | +34.5 |
| 67 | C=O | $Z^2$ = OH, $Z^6$ = F | 240–252 | racemate |
| 68 | C=O | $Z^2$ = OH, $Z^4$ = Br | 248–250 | racemate |
| 69 | C=O | $Z^2$ = OH, $Z^4$ = Br | 249–251 | +20.0 (c = 0.5, THF) |

(1) The optically active compounds that are presented in the table were separated analogously to Example 1. Unless otherwise indicated, the measurement was made in methanol.

Example 70

Process 5

5-[4-(2-Ethoxy-5-fluorophenyl)-2-hydroxy-4-methyl-2-trifluoromethyl-valeroylamino]-phthalide 44 mg of 5-[4-(5-fluoro-2-hydroxyphenyl)-2-hydroxy-4-methyl-4-2-trifluoromethyl-valeroyl-amino]-phthalide is stirred in 1 ml of dimethylformamide with 28 mg of potassium carbonate and 50 mg of ethyl iodide for 24 hours at room temperature. It is then mixed with water, extracted with ethyl acetate, the organic phase is washed with water, dried ($Na_2SO_4$) and after the solvent is concentrated by evaporation, 35 mg of 5-[4-(2-ethoxy-5-fluorophenyl)-2-hydroxy-4-methyl-2-trifluoromethyl-valeroylamino]-phthalide is obtained, flash point 108° C.

The compounds of Table 6 were produced analogously to the example above.

TABLE 6

| Example | R | Reagent | Flash Point (° C.) | Isomerism or $[\alpha]_D$ (c = 0.5) (1) |
|---|---|---|---|---|
| 71 | $CH(CH_3)_2$ | $BrCH(CH_3)_2$ | 153–154 | racemate |
| 72 | $CH_2CH=CH_2$ | $BrCH_2CH=CH_2$ | 152 | racemate |
| 73 | $CH_2CH=CH$ | $BrCH_2CH=CH$ | 187–189 | racemate |
| 74 | $CH_2Ph$ | $BrCH_2Ph$ | 93 | racemate |
| 75 | $CH_2CN$ | $BrCH_2CN$ | 170–172 | racemate |
| 76 | $CH_2COOC-(CH_3)_3$ | $BrCH_2COOC-(CH_3)_3$ | 145 | racemate |
| 77 | $CH_2COOC-(CH_3)_3$ | $BrCH_2COOC-(CH_3)_3$ | 143 | −131.5 |
| 78 | $CH_2COOC-(CH_3)_3$ | $BrCH_2COOC-(CH_3)_3$ | 142—143 | +132 |
| 79 | $CHF_2$ | $ClCF_2COOH$ | 163 | racemate |
| 80 | $CH_2OCH_3$ | $ClCH_2OCH_3$ | 126–127 | racemate |
| 81 | $CH_2OC_2H_5$ | $ClCH_2OC_2H_5$ | 113–114 | racemate |
| 82 | $CH_2CH_2OCH_3$ | $ClCH_2CH_2-OCH_3$ | 168–169 | racemate |

(1) The optically active compounds that are presented in the table were separated analogously to Example 1. Unless otherwise indicated, the measurement was made in methanol.

Example 83

(−)-4-Bromo-5-[4-(5-fluoro-2-hydroxyphenyl)-2-hydroxy-4-methyl-2-trifluoromethyl-pentylamino]-phthalide 55 mg of (−)-5-[4-(5-fluoro-2-hydroxyphenyl)-2-hydroxy-4-methyl-2-trifluoromethyl-pentylamino]-phthalide is mixed under nitrogen in 1 ml of dimethylformamide at 2° C. with 18 mg of N-bromosuccinimide. After 2 hours at this temperature, it is diluted with 20 ml of ethyl acetate, extracted with water, and the organic phase is dried ($Na_2SO_4$) and concentrated by evaporation. With chromatography on silica gel, the title compound in crystalline form is eluted with hexane/ethyl acetate (4:1), flash point 228–232° C.

Example 84

(−)-4-Bromo-5-[4-(3-bromo-5-fluoro-2-hydroxyphenyl)-2-hydroxy-4-methyl-2-trifluoromethyl-pentylamino]-phthalide If 44 mg of N-bromosuccinimide is used in the preceding example on 100 mg of (−)-5-[4-(5-fluoro-2-hydroxyphenyl)-2-hydroxy-4-methyl-2-trifluoromethyl-pentylamino]-phthalide, the title compound is obtained in crystalline form after chromatography on silica gel with hexane/ethyl acetate (7:3), flash point 144–146° C.

Example 85

5-[4-(2,3-Dihydro-7-benzofuranyl-2-hydroxy-4-methyl-2-trifluoromethyl-pentanoyl-amino]-phthalide is obtained from 5-[4-(2,3-dihydro-7-benzofuranyl-4-methyl-2-oxo-pentanoyl-amino]-phthalide analogously to Example 1, flash point 182–185° C.

Example 86

6-[4-(2,3-Dihydro-7-benzofuranyl-2-hydroxy-4-methyl-2-trifluoromethyl-pentanoyl-amino]-4-methyl-2,3-benzoxazin-1-one is obtained from 6-[4-(2,3-dihydro-7-benzofuranyl-4-methyl-2-oxo-pentanoyl-amino]-4-methyl-2,3-benzoxazin-1-one analogously to Example 1, flash point 215–220° C.

Pharmacological Examples

In the glucocorticoid receptor (GR)-binding test with use of cytosol preparations that consist of the thymus homogenates of rats and of 10 nM of [$^3$H]-dexamethasone as a reference substance (cf. Lefebvre et al. J. Steroid. Biochem., 33, 557–563, 1989), the compounds of formula 1 show a high to very high affinity to the GR (see Table).

| Table of GR-Values | |
|---|---|
| Compound | IC50 mol/l |
| i | $2.8 \cdot e^{-9}$ |
| ii | $2.3 \cdot e^{-9}$ |
| iii | $4.6 \cdot e^{-9}$ |
| iv | $4.9 \cdot e^{-9}$ |
| v | $2.6 \cdot e^{-9}$ |
| dexamethasone | $2.0 \cdot e^{-8}$ |

The compounds that are mentioned in the table are the following especially preferred compounds:

i: 5-[4-(5-Fluoro-2-hydroxyphenyl)-2-hydroxy-4-methyl-2-trifluoromethyl-valeroylamino]-phthalide ii: 5-[4-(5-fluoro-2-hydroxyphenyl)-2-hydroxy-4-methyl-2-trifluoromethyl-pentylamino]-phthalide iii: 6-[4-(5-fluoro-2-methoxyphenyl)-2-hydroxy-4-methyl-2-trifluoromethyl-valeroylamino]-4-methyl-2,3-benzoxazin-1-one iv: 6-[4-(4-bromo-2-methoxyphenyl)-2-hydroxy-4-methyl-2-trifluoromethyl-valeroylamino]-4-methyl-2,3-benzoxazin-1-one v: 6-[4-(5-fluoro-2-hydroxyphenyl)-2-hydroxy-4-methyl-2-trifluoromethyl-valeroylamino]-4-methyl-2,3-benzoxazin-1-one The compounds of general formula I according to the invention inhibit the secretion of cytokines IL-8 and TNF-α in human monocyte cell line THP-1 that is trigggered by phorbol ester and ionomycin. The concentration of the cytokines was determined in the supernatant by means of commercially available ELISA kits (cf. Welker et al., Int. Arch. Allergy Immunol., 109, 110–115, 1996). At a concentration of 1 μM, the compounds show a maximum inhibition of cytokine secretion by 50–80%. The anti-inflammatory actions of the compounds of general formula I were tested in the animal experiment by testing in the croton oil-induced inflammation in rats and mice (cf. Tubaro et al., Agents Actions, 17, 347–349, 1985). In this respect, croton oil in an ethanolic solution was administered topically to the ears in the animals. The test substances were also topically or systemically administered simultaneously or two hours before the croton oil. After 16–24 hours, the ear weight was measured as a measurement of the inflammatory edema, the peroxidase activity was measured as a measurement for the invasions of granuloctyes, and the elastase activity was measured as a measurement for the invasions of neutrophilic granuloctyes. In this test, the compounds of general formula I inhibit the three above-mentioned inflammation parameters both after topical administration and after systemic administration.

To measure the TAT induction, the animals are sacrificed 6 hours after the test substances are administered, the livers are removed, and the TAT activity in the homogenate is measured (cf. Diamandstone et al. Anal. Biochemistry, 16, 395–401, 1966). At a dose of 10–30 mg/kg of body weight, the compounds inhibited the ear inflammation by about 50–80% and induced in this dose range the tyrosinamino transferase in the liver of the animals by 0–4 times the starting value. Since the substances of the general formula also have a high affinity to the progesterone receptor, the new compounds were tested for their gestagenic action in the animal experiment. For this purpose, the pregnancy-maintenance test was performed on ovariectomized rats (cf. Neumann et al. Arzneim. Forsch. (Drug Res.), 34, 296–318, 1984). In this respect, female rats are covered and undergo ovariectomy under anesthesia on day eight of the pregnancy two hours after substance administration. From day 8–14 of the pregnancy, the animals are treated daily with the test substances, and on day 15, the animals are sacrificed, and the number of living and dead fetuses per animal is determined. In the case of empty uteri, the number of implantation sites is determined by staining with 10% ammonium sulfide solution. The new compounds of formula I resulted in little or no maintenance of pregnancy up to a dose of 500 μg per kg of body weight. In dosages up to 500 μg/kg of body weight, the new compounds of general formula I have little to no gestagenic action.

In particular, the following compounds show an especially effective pharmaceutical action:

5-[4-(5-Fluoro-2-hydroxyphenyl)-2-hydroxy-4-methyl-2-trifluoromethyl-valeroylamino]-phthalide 5-[4-(5-fluoro-2-hydroxyphenyl)-2-hydroxy-4-methyl-2-trifluoromethyl-pentylamino]-phthalide 6-[4-(5-fluoro-2-methoxyphenyl)-2-hydroxy-4-methyl-2-trifluoromethyl-valeroylamino]-4-methyl-2,3-benzoxazin-1-one 6-[4-(4-bromo-2-methoxyphenyl)-2-hydroxy-4-methyl-2-trifluoromethyl-valeroylamino]-4-methyl-2,3-benzoxazin-1-one 6-[4-(5-fluoro-2-hydroxyphenyl)-2-hydroxy-4-methyl-2-trifluoromethyl-valeroylamino]-4-methyl-2,3-benzoxazin-1-one Because of their anti-inflammatory and additional antiallergic, immunosuppressive and anti-proliferative actions, the compounds of general formula I according to the invention can be used as medications for treatment or prophylaxis of the following pathologic conditions in mammals and humans: In this case, the term "DISEASE" stands for the following indications:

Indications, which coincide with inflammatory, allergic and/or proliferative processes:

(i) Lung diseases
(ii) Rheumatic diseases/auto-immune diseases/
(iii) Allergies
(iv) Dermatological diseases
(v) Nephropathies
(vi) Liver diseases
(vii) Gastrointestinal diseases
(viii) Protocological diseases
(ix) Eye diseases
(x) Diseases of the ear-nose-throat area
(xi) Neurological diseases
(xii) Blood diseases
(xiii) Tumor diseases
(xiv) Endocrine diseases
(xv) Transplants
(xvi) Severe shock conditions
(xvii) Substitution therapy with suprarenal insufficiency
(xviii) Emesis.

The compounds of general formula I according to the invention can also be used for therapy and prophylaxis of additional pathologic conditions that are not mentioned above, for which synthetic glucocorticoids are now used (see in this connection Hatz, H. J., Glucocorticoide: Immunologische Grundlagen, Pharmakologie und Therapierichtlinien, Wissenschaftliche Verlagsgesellschaft mbH, Stuttgart, 1998).

For the therapeutic actions in the above-mentioned pathologic conditions, the suitable dose is different and it depends on, for example, the active strength of the compound of general formula I, the host, the type of administration and the type and severity of the conditions that are to be treated, as well as the use as prophylactic agent or therapeutic agent.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of achieving an anti-inflammatory effect in a host in need thereof, comprising administering a compound of formula I

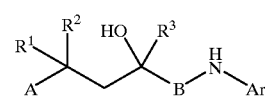

in which
$R^1$ and $R^2$ are each independently a hydrogen atom, a $C_1$–$C_5$ alkyl group, or, together with the C-atom of the chain, $R^1$ and $R^2$ stand for a ring with a total of 3–7 links,
$R^3$ stands for a $C_1$–$C_5$ alkyl group or a partially or completely fluorinated $C_1$–$C_5$ alkyl group, A stands for the group

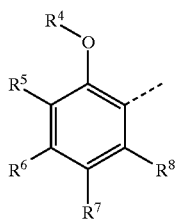

(the dashed line means the interface site), in which
$R^4$ means a hydrogen atom, a $C_1$–$C_5$ alkyl group, a $C_1$–$C_{10}$ acyl group, a $C_3$–$C_{10}$ carbalkoxyalkyl group, a $C_{2-C5}$ cyanoalkyl group, a $C_3$–$C_{10}$ unsubstituted or substituted allyl group, a $C_3$–$C_{10}$ unsubstituted or substituted propargyl group, a $C_2$–$C_5$ alkoxyalkyl group, a $C_1$–$C_5$ alkyl group that is partially or completely substituted by fluorine atoms, $R^5$ to $R^8$ are the same or different from one another and are hydrogen or halogen atoms or $C_1$–$C_5$ alkoxy groups, and $R^4$ and $R^5$ together mean a heterocyclic ring, which in addition to the oxygen atom optionally can contain at least one other heteroatom from the group of oxygen, nitrogen, sulfur, with a total of 5–7 links, B stands for a carbonyl group or a $CH_2$ group, and
Ar stands for a ring system of partial formulas 2–5,

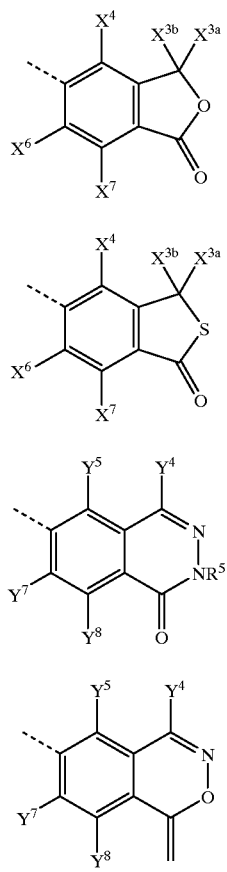

in which
radicals $X^{3a}$, $X^{3b}$, $X^4$, $X^6$, $X^7$ in partial formulas 2 and 3 and $Y^4$, $Y^5$, $Y^7$, and $Y^8$ in partial formulas 4 and 5 each independently hydrogen atoms, $C_1$–$C_5$ alkyl groups, or partially or completely fluorinated $C_1$–$C_5$ alkyl groups, and radicals $X^4$, $X^6$, $X^7$ in partial formulas 2 and 3 or $Y^5$, $Y^7$, $Y^8$ in partial formulas 4 and 5 are each independently halogen atoms, hydroxy groups, $C_1$–$C_5$ alkoxy groups or $C_1$–$C_5$ alkanoyloxy groups, or, if B stands for a $CH_2$ group, physiologically compatible acid salts of compounds of formula I.

2. A method according to claim 1 the said anti-inflammatory effect is achieved in (i) Lung diseases,
(ii) Rheumatic disease,
(iii) Allergies,
(iv) Dermatological diseases,
(v) Nephropathies,
(vi) Liver diseases,
(vii) Gastrointestinal diseases,
(viii) Proctological diseases,
(ix) Eye diseases,
(x) Diseases of the ear-nose-throat area,
(xi) Neurological diseases,
(xii) Blood diseases,
(xiii) Tumor diseases,
(xiv) Endocrine diseases,
(xv) Transplant complications,
(xvi) Severe shock conditions,
(xvii) Suprarenal insufficiency in substitution therapy,
(xviii) Emesis,
    and/or
(xix) auto-immune diseases.

3. A method according to claim 1 wherein the compound of formula I is administered in the form of a racemate.

4. A method according to claim 1 wherein the compound of formula I is administered in the form of separate stereoisomers.

5. A method according to claim 1, wherein $C_1$–$C_5$ alkyl group(s) in the compound of formula I are independently methyl, ethyl, n-propyl, iso-propyl, n-, iso- or tert-butyl, n-pentyl, 2,2-dimethylpropyl or 3-methylbutyl.

6. A method according to claim 1, wherein halogen atom $Y^5$, $Y^7$, and $Y^8$ are each independently fluorine, chlorine or bromine.

7. A method according to claim 1, wherein $R^1$ and $R^2$ together with the C-atom of the chain form a cyclopropyl, cyclobutyl, cyclopentyl or cyclohexyl ring.

8. A method according to claim 1, wherein completely fluorinated alkyl groups are perfluorinated methyl, ethyl, n-propyl, iso-propyl, n-, iso- or tert-butyl, n-pentyl, 2,2-dimethylpropyl or 3-methylbutyl groups.

9. A method according to claim 1, wherein partially fluorinated $C_{1-5}$ alkyl group is 5,5,5,4,4-pentafluoropentyl or 5,5,5,4,4,3,3-heptafluoropentyl.

10. A method according to claim 1, wherein $C_{3-10}$-carbalkonyl is carboxymethyl, tert-butoxymethyl or ethoxymethyl group.

11. A method according to claim 1, wherein $C_{2-5}$-cyanoalkyl is cyanomethyl, or 1- or 2-cyanoethyl.

12. A method according to claim 1, wherein $C_{3-10}$-allyl is an unsubstituted allyl group, a 1-methylallyl, 1,1-dimethylallyl, 2-methylallyl, 3-methylallyl, 2,3-dimethylallyl, 3,3-dimethylallyl, cinnamyl or 3-cyclohexylallyl group.

13. A method according to claim 1, wherein $C_{3-10}$-propargyl is an unsubstituted propargyl group, a methylpropargyl group, 3-methylpropargyl group, 3-phenylpropargyl group or 3-cyclohexylpropargyl group.

14. A method according to claim 1, wherein $C_{2-5}$-alkoxyalkyl is methoxymethyl group, ethoxymethyl group or 2-methylethyl group.

15. A method according to claim 1, wherein $C_{1-5}$-alkoxy is methoxy, ethoxy, n-propoxy, iso-propoxy, n-, iso- or tert-butoxy or n-pentoxy, 2,2-dimethylpropoxy or 3-methylbutoxy.

16. A method according to claim 1, wherein $C_{1-5}$-perfluoroalkoxy is perfluorinated methoxy, ethoxy, n-propoxy, iso-propoxy, n-, iso- or tert-butoxy, or n-pentoxy, 2,2-dimethylpropoxy, or 3-methylbutoxy group.

17. A method according to claim 1, wherein $C_{1-5}$-alkanoyl is formyl, acetyl, propionyl, butyryl, iso-butyryl, valeryl or iso-valeryl or pivaloyl group.

18. A method according to claim 1, wherein $C_{1-10}$-aryl is benzoyl, toluoyl, phenylacetyl, acryloyl, cinnamoyl or cyclohexylcarbonyl group.

19. A method according to claim 1, wherein $C_{1-5}$-alkamoyloxy $X^4$, $X^6$, $X^7$, $Y^4$, $Y^5$, $Y^7$ or $Y^8$ is formyloxy, acetoxy, propionyloxy, butyryloxy, iso-butyryloxy, valeryloxy or iso-valeryloxy group.

20. A method according to claim 1, wherein if B=—CH$_2$- the compound of formula I is a hydrochloride, sulfate, nitrate, maleate, fumarate, tartrate or benzoate salt.

21. A method according to claim 1, wherein in the compound of formula I
   $R^1$ and $R^2$ are each independently a hydrogen atom, a methyl or ethyl group; or together with the C-atom of the chain, $R^1$ and $R^2$ are a cyclopropyl ring, and/or
   $R^3$ is a $C_1$–$C_5$ perfluoroalkyl group, and/or
   A is

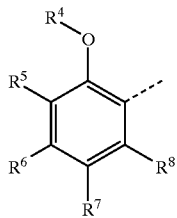

in which
   $R^4$ means a hydrogen atom, a methyl, ethyl, propyl or 2-propyl group, an acety group, a methoxy, ethoxy or tert-butoxycarbonyl group, a cyanomethyl group, a 2-cyanoethyl group, an allyl group, a propargyl group, a methoxymethyl, methoxyethyl or ethoxyethyl group, a mono-, di- or trifluoromethyl group, a pentafluoroethyl or nanofluorobutyl group,
   $R^5$ to $R^8$ in one or two positions is fluorine or chlorine atoms and in remaining positions is hydrogen,
   or
   $R^4$ and $R^5$ together with incorporation of phenyl-ring atoms 2 and 3 is a furan, a dihydrofuran or a 2,3-dihydro-1,4-dioxine ring and $R^6$, $R^7$ and $R^8$ are hydrogen atoms,
   $X^{3a}$ is a hydrogen atom or a methyl group, or
   $X^{3a}$ and $X^{3b}$ are each independently a hydrogen atom or a methyl group,
   $X^4$, $X^6$ and $X^7$ are each independently a hydrogen atom or a fluorine or a chlorine atom,
   and/or
   $Y^4$ is a methyl, ethyl, propyl, 2-propyl or trifluoromethyl group and/or
   $Y^5$, $Y^7$ and $Y^8$ are, each independently a hydrogen atom or a fluorine atom or a chlorine atom.

22. A method according to claim 1, wherein Ar stands for a ring system of partial formula 2 or 5.

23. A method according to claim 1 wherein the compound of formula I is

5-{2-Hydroxy-3-[1-(2-methoxyphenyl)-cyclopropyl]-2-trifluoromethyl-propionylamino}-phthalide,
5-{3-[1-(5-fluoro-2-methoxyphenyl)-cyclopropyl]-2-hydroxy-2-trifluoromethyl-propionylamino}-phthalide,
5-[2-hydroxy4-(2-methoxyphenyl)-4-methyl-2-trifluoromethyl-valeroylamino]-phthalide,
5-{3-[1-(5-fluoro-2-hydroxyphenyl)-cyclopropyl]-2-hydroxy-2-trifluoromethyl-propionylamino}-phthalide,
5-[4-(5-fluoro-2-hydroxyphenyl)-2-hydroxy-4-methyl-2-trifluoromethyl-valeroylamino]-phthalide
5-[4-(5-fluoro-2-hydroxyphenyl)-2-hydroxy-4-methyl-2-trifluoromethyl-pentylamino]-phthalide,
4-bromo-5-[4-(5-fluoro-2-hydroxyphenyl)-2-hydroxy-4-methyl-2-trifluoromethyl-pentylamino]-phthalide,
4-bromo-5-[4-(3-bromo-5-fluoro-2-hydroxyphenyl)-2-hydroxy-4-methyl-2-trifluoromethyl-pentylamino]-phthalide,
6-{3-[1-(5-fluoro-2-hydroxyphenyl)-cyclopropyl]-2-hydroxy-2-trifluoromethyl-propionylamino}-4-methyl-2,3-benzoxazin-1-one,
6-[4-(5-fluoro-2-methoxyphenyl)-2-hydroxy-4-methyl-2-trifluoromethyl-valeroylamino]-4-methyl-2,3-benzoxazin-1-one,
6-[4-(5-fluoro-2-hydroxyphenyl)-2-hydroxy-4-methyl-2-trifluoromethyl-valeroylamino]-4-methyl-2,3-benzoxazin-1-one,
6-[2-hydroxy-4-(2-hydroxyphenyl)-4-methyl-2-trifluoromethyl-valeroylamino]-4-ethyl-2,3-benzoxazin-1-one,
6-[4-(5-fluoro-2-methoxyphenyl)-2-hydroxy-4-methyl-2-trifluoromethyl-pentylamino]-4-methyl-2,3-benzoxazin-1-one,
6-[4-(5-fluoro-2-hydroxyphenyl)-2-hydroxy-4-methyl-2-trifluoromethyl-pentylamino]4-methyl-2,3-benzoxazin-1-one,
6-[4-(4-bromo-2-methoxyphenyl)-2-hydroxy-4-methyl-2-trifluoromethyl-valeroylamino]-4-methyl-2,3-benzoxazin-1-one,
6-[4-(4-bromo-2-methoxyphenyl)-2-hydroxy-4-methyl-2-trifluoromethyl-pentylamino]-4-methyl-2,3-benzoxazin-1-one.

24. A compound is
5-{3-[1-(5-Fluoro-2-methoxyphenyl)-cyclopropyl]-2-hydroxy-2-trifluoromethyl-propionylamino}-phthalide,
5-{3-[1-(5-fluoro-2-hydroxyphenyl)-cyclopropyl]-2-hydroxy-2-trifluoromethyl-propionylamino}-phthalide,
4-bromo-5-[4-(5-fluoro-2-hydroxyphenyl)-2-hydroxy-4-methyl-2-trifluoromethyl-pentylamino]-phthalide,
4-bromo-5-[4-(3-bromo-5-fluoro-2-hydroxyphenyl)-2-hydroxy-4-methyl-2-trifluoromethyl-pentylamino]-phthalide,
6-{3-[1-(5-fluoro-2-hydroxyphenyl)-cyclopropyl]-2-hydroxy-2-trifluoromethyl-propionylamino}-4-methyl-2,3-benzoxazin-1-one,
6-[2-hydroxy-4-(2-hydroxyphenyl)-4-methyl-2-trifluoromethyl-valeroylamino]-4-ethyl-2,3-benzoxazin-1-one,
6-[4-(4-bromo-2-methoxyphenyl)-2-hydroxy-4-methyl-2-trifluoromethyl-pentylamino]-4-methyl-2,3-benzoxazin-1-one, 5-{3-[1-(5-fluoro-2-methoxyphenyl)-cyclopropyl]-2-hydroxy-2-trifluoromethyl-propionylamino}-phthalide, 6-[2-hydroxy-4-(5-fluoro-2-methoxyphenyl)-4-methyl-2-trifluoromethyl-pentylamino]-4-methyl-2,3-benzoxazin-1-one, 5-{3-[1-(5-fluoro-2-hydroxyphenyl)-cyclopropyl]-2-hydroxy-2-trifluoromethyl-propionylamino}-phthalide, 6-{3-[1-(5-fluoro-2-hydroxyphenyl)-cyclopropyl]-2-hydroxy-2-trifluoromethyl-propionylamino}-4-methyl-2,3-benzoxazin-1-one, (−)-4-bromo-5-[4-(5-fluoro-2-hydroxyphenyl)-2-hydroxy-4-methyl-2-trifluoromethyl-pentylamino]-phthalide, (−)-4-bromo-5-[4-(3-bromo-5-fluoro-2-hydroxyphenyl)-2-hydroxy-4-methyl-2-trifluoromethyl-pentylamino]-phthalide, 5-[2-hydroxy-4-(5-isopropyl-2-methoxyphenyl)-4-methyl-2-trifluoromethyl-valeroylamino]-phthalide, 5-[2-hydroxy-4-(2-methoxy-5-propyl-phenyl)-4-methyl-2-trifluoromethyl-valeroylamino]-phthalide, 5-[2-hydroxy-4-(2-benzyloxy-5-fluorophenyl)-4-methyl-2-trifluoromethyl-valeroylamino]-phthalide, 5-[2-hydroxy-4-(2-difluoromethoxy-5-fluorophenyl)-4-methyl-2-trifluoromethyl-valeroylamino]-phthalide, 5-[2-hydroxy-4-(5-fluoro-2-methoxymethoxy-phenyl)-4-methyl-2-trifluoromethyl-valeroylamino]-phthalide, 5-[2-hydroxy-4-(2-ethoxymethoxy-5-fluorophenyl)-4-methyl-2-trifluoromethyl-valeroylamino]-phthalide, or 5-{[2-hydroxy-4-[5-fluoro-2-(2-methoxyethoxy)-phenyl]-4-methyl-2-trifluoromethyl-valeroylamino}-phthalide.

25. A pharmaceutical composition comprising at least one compound of formula I according to claim 24, and a pharmaceutically compatible vehicle.

26. A process for the preparation of a composition according to claim 25, comprising mixing a compound of formula I' and a pharmaceutically compatible vehicle.

\* \* \* \* \*

UNITED STATES PATENT AND TRADEMARK OFFICE
CERTIFICATE OF CORRECTION

PATENT NO. : 6,323,199 B1
DATED : November 27, 2001
INVENTOR(S) : Lehmann et al.

It is certified that error appears in the above-identified patent and that said Letters Patent is hereby corrected as shown below:

Title page,
Item [57], ABSTRACT,
Delete last word in the ABSTRACT "action" and insert -- actions --.

Column 29,
Line 16, delete "$C_2$-$C_5$" and insert -- $C_2$-$C_5$ --.

Signed and Sealed this

Eighteenth Day of February, 2003

JAMES E. ROGAN
*Director of the United States Patent and Trademark Office*